US009287729B2

(12) United States Patent
Nyu et al.

(10) Patent No.: US 9,287,729 B2
(45) Date of Patent: Mar. 15, 2016

(54) SECONDARY BATTERY STATE MANAGEMENT SYSTEM, BATTERY CHARGER, SECONDARY BATTERY STATE MANAGEMENT METHOD, AND ELECTRICAL CHARACTERISTICS MEASUREMENT METHOD

(75) Inventors: Takayuki Nyu, Tokyo (JP); Akira Inoue, Tokyo (JP); Shuntaro Yamazaki, Tokyo (JP)

(73) Assignee: NEC CORPORATION, Tokyo (JP)

( * ) Notice: Subject to any disclaimer, the term of this patent is extended or adjusted under 35 U.S.C. 154(b) by 568 days.

(21) Appl. No.: 13/643,230

(22) PCT Filed: Apr. 22, 2011

(86) PCT No.: PCT/JP2011/002358
§ 371 (c)(1),
(2), (4) Date: Dec. 21, 2012

(87) PCT Pub. No.: WO2011/135813
PCT Pub. Date: Nov. 3, 2011

(65) Prior Publication Data
US 2013/0093384 A1    Apr. 18, 2013

(30) Foreign Application Priority Data

Apr. 26, 2010  (JP) ................................. 2010-101223

(51) Int. Cl.
*H02J 7/00* (2006.01)
*H02J 7/04* (2006.01)
(Continued)

(52) U.S. Cl.
CPC ........... *H02J 7/0052* (2013.01); *B60L 11/1838* (2013.01); *G01R 31/3606* (2013.01);
(Continued)

(58) Field of Classification Search
CPC ................ H02J 7/00; H02J 7/04; H02J 7/24; H02J 7/06; H02J 7/0052; H02J 7/0027; H02J 7/0004; H02J 2007/0001; G01N 27/416; H01M 10/44; B60L 11/1838; B60L 2240/545; B60L 2240/547; B60L 2240/549; B60L 2250/16; G01R 31/3606; G01R 31/3651; Y02T 10/7005; Y02T 10/7055; Y02T 90/121; Y02T 90/128; Y02T 90/14; Y02T 90/163; Y02T 90/168; Y02T 30/12; Y04S 30/12
USPC ......... 320/107, 132, 136, 147, 149, 162, 164; 324/433
See application file for complete search history.

(56) References Cited

U.S. PATENT DOCUMENTS 4,433,294 A  *  2/1984  Windebank ................... 324/426
4,958,127 A  *  9/1990  Williams ............. G01R 31/362
320/132
(Continued)

FOREIGN PATENT DOCUMENTS

JP          3-182063 A       8/1991
JP          6-38394 A        2/1994
(Continued)

OTHER PUBLICATIONS

Vetter et al., German Patent Publication No. DE019903239A1, front page only.*
(Continued)

*Primary Examiner* — Phallaka Kik
(74) *Attorney, Agent, or Firm* — Sughrue Mion, PLLC

(57) ABSTRACT

A secondary battery state management system of the present invention includes: a battery charger that charges a secondary battery; and a storage server that stores electrical characteristics information which is information that indicates the electrical characteristics during charging of the secondary battery. An electrical characteristics measuring means measures the electrical characteristics during charging. A measurement information storing means stores the history of the measured electrical characteristics information for each secondary battery. A battery state determining means compares the electrical characteristics information of the secondary battery being measured by the electrical characteristics measuring means with the electrical characteristics information of the same secondary battery stored in the measurement information storing means, and determines the state of the secondary battery.

26 Claims, 14 Drawing Sheets

(51) Int. Cl.
*H02J 7/24* (2006.01)
*H02J 7/06* (2006.01)
*H01M 10/44* (2006.01)
*G01N 27/416* (2006.01)
*B60L 11/00* (2006.01)
*G01R 31/36* (2006.01)
*B60L 11/18* (2006.01)

(52) U.S. Cl.
CPC ......... *H02J7/0027* (2013.01); *B60L 2240/545* (2013.01); *B60L 2240/547* (2013.01); *B60L 2240/549* (2013.01); *B60L 2250/16* (2013.01); *G01N 27/416* (2013.01); *G01R 31/3651* (2013.01); *H01M 10/44* (2013.01); *H02J 7/0004* (2013.01); *H02J 2007/0001* (2013.01); *Y02T 10/7005* (2013.01); *Y02T 10/7055* (2013.01); *Y02T 90/121* (2013.01); *Y02T 90/128* (2013.01); *Y02T 90/14* (2013.01); *Y02T 90/163* (2013.01); *Y02T 90/168* (2013.01); *Y04S 30/12* (2013.01)

(56) References Cited

U.S. PATENT DOCUMENTS

| | | | | |
|---|---|---|---|---|
| 5,280,232 | A * | 1/1994 | Kohl | H02J 7/166 320/137 |
| 5,479,085 | A * | 12/1995 | Honda | G01R 31/361 320/134 |
| 5,508,598 | A * | 4/1996 | Al-Abassy | 320/129 |
| 5,661,463 | A * | 8/1997 | Letchak et al. | 340/636.15 |
| 5,663,629 | A * | 9/1997 | Hinohara | H02J 7/0073 320/158 |
| 5,717,312 | A * | 2/1998 | Maeda | G01R 19/16542 320/162 |
| 6,049,193 | A * | 4/2000 | Chien | H02J 7/0077 320/128 |
| 6,664,764 | B1 * | 12/2003 | Odaohhara | 320/132 |
| 7,710,075 | B1 * | 5/2010 | Kilbourne et al. | 320/134 |
| 2002/0033693 | A1 * | 3/2002 | Kohler | 320/152 |
| 2002/0120906 | A1 * | 8/2002 | Xia et al. | 716/2 |
| 2004/0095096 | A1 * | 5/2004 | Melton et al. | 320/132 |
| 2005/0110466 | A1 * | 5/2005 | Shoji | G01R 31/3624 320/150 |
| 2005/0269991 | A1 * | 12/2005 | Mitsui | G01R 31/3624 320/132 |
| 2006/0055374 | A1 * | 3/2006 | Fujihara | G01R 31/3651 320/132 |
| 2006/0164043 | A1 * | 7/2006 | Ukon | G01R 19/16542 320/162 |
| 2006/0192564 | A1 * | 8/2006 | Brown et al. | 324/426 |
| 2007/0072014 | A1 * | 3/2007 | Kim et al. | 429/7 |
| 2007/0114971 | A1 * | 5/2007 | Uesaka | G01R 31/3624 320/132 |
| 2008/0150491 | A1 * | 6/2008 | Bergveld | G01R 31/361 320/139 |
| 2009/0212781 | A1 * | 8/2009 | Bertness et al. | 324/426 |
| 2009/0243550 | A1 * | 10/2009 | Arai | H02J 7/1492 320/157 |
| 2009/0295399 | A1 * | 12/2009 | Ueda | B60L 11/1859 324/429 |
| 2010/0010704 | A1 * | 1/2010 | Uchida | 701/32 |
| 2010/0127710 | A1 * | 5/2010 | Hasegawa et al. | 324/433 |
| 2010/0201323 | A1 * | 8/2010 | Okamura | H02J 7/0072 320/134 |
| 2010/0237873 | A1 * | 9/2010 | Franke et al. | 324/434 |
| 2011/0072280 | A1 * | 3/2011 | Chiasson et al. | 713/300 |
| 2011/0273181 | A1 * | 11/2011 | Park et al. | 324/429 |
| 2011/0298626 | A1 * | 12/2011 | Fechalos | H01M 10/482 340/664 |

FOREIGN PATENT DOCUMENTS

| | | | |
|---|---|---|---|
| JP | 8-37036 A | 2/1996 | |
| JP | 8-273705 A | 10/1996 | |
| JP | 11-052033 A | 2/1999 | |
| JP | 2000-131404 A | 5/2000 | |
| JP | 2000215923 A * | 8/2000 | ............ H01M 10/48 |
| JP | 2006-172884 A | 6/2006 | |
| JP | 2007-166789 A | 6/2007 | |
| JP | 2007-336778 A | 12/2007 | |
| JP | 2010-22155 A | 1/2010 | |

OTHER PUBLICATIONS

Yoshiyuki, Machine Translation of Japanese Patent Publication No. 06-038394, published Oct. 2, 1994, machine translated on Apr. 18, 2015 by Japanese Patent Office machine translation, 10 pages.*
Takeno Kazuhiko, et al., "Capacity Deterioration Characteristics of Lithium-Ion Batteries for Mobile Phones", NTT DoCoMo Technical Journal, 4 pages, vol. 13, No. 4.
Communication dated Nov. 11, 2014 from the Japanese Patent Office in counterpart application No. 2012-512656.

* cited by examiner

SECONDARY BATTERY STATE MANAGEMENT SYSTEM, BATTERY CHARGER, SECONDARY BATTERY STATE MANAGEMENT METHOD, AND ELECTRICAL CHARACTERISTICS MEASUREMENT METHOD

CROSS REFERENCE TO RELATED APPLICATIONS

This application is a National Stage of International Application No. PCT/JP2011/002358, filed on Apr. 22, 2011, which claims priority from Japanese Patent Application No. 2010-101223, filed on Apr. 26, 2010, the contents of all of which are incorporated herein by reference in their entirety.

TECHNICAL FIELD

The invention relates to a secondary battery state management system that manages the state of a secondary battery mounted on an electric-powered vehicle or the like, a battery charger, a secondary battery state management method, an electrical characteristics measurement method, and an electrical characteristics measurement program.

BACKGROUND ART

An electric car and a hybrid car on which both an internal combustion engine and a motor are mounted are examples of an electric-powered vehicle on which a secondary battery is mounted. In order to drive such an electric-powered vehicle with electricity, it is necessary to charge the mounted secondary battery from an external battery charger. When charging the secondary battery, it is generally necessary to perform charging control according to the characteristics unique to the battery.

Moreover, when a secondary battery is used for a long period of time, charging and discharging may be performed repeatedly. When charging and discharging is performed repeatedly, the performance of the secondary battery deteriorates, and depending on the deterioration condition, the secondary battery may generate heat and may catch fire. In order to prevent the user of the secondary battery from having severe damage, when using the secondary battery, it is necessary to monitor the deterioration state and perform charging control according to the characteristics of the secondary battery.

Patent Literature 1 discloses a secondary battery system in which a secondary battery is provided with a function of storing the information unique to the secondary battery. The secondary battery system disclosed in Patent Literature 1 notifies the unique information to an external apparatus. When the external apparatus is a battery charger, the battery charger controls charging according to the unique information of the secondary battery, acquired from the secondary battery system.

Patent Literature 2 discloses a charging system that performs charging according to the charging characteristics of a battery. In the charging system disclosed in Patent Literature 2, rather than notifying the battery charger of the unique information of the secondary battery, a reference charging value such as a voltage value or a current value is calculated by taking the unique information of the secondary battery into consideration, and the reference value is notified to the battery charger. Moreover, the battery charger performs charging control of outputting a voltage or a current according to the reference charging value sent from the battery system.

Moreover, Patent Literature 3 discloses a charging device for secondary batteries. The charging device disclosed in Patent Literature 3 detects a terminal voltage of a secondary battery every predetermined intervals of time as the state of the secondary battery, calculates the latest slope and the average slope of a charging curve that indicates a change of the terminal voltage, and determines whether a charging current will be supplied or stopped.

Non Patent Literature 1 discloses a change of the battery performance with charging and discharging. Non Patent Literature 1 states that repeated charging and discharging leads to decrease battery capacity and change charging and discharging characteristics. Moreover, Non Patent Literature 1 also states that the internal impedance of the secondary battery increases when the battery capacity decreases.

CITATION LIST

Patent Literature

PLT 1: Japanese Patent Application Laid-Open (JP-A) No. 8-37036 (Paragraphs 0001 and 0022)
PLT 2: JP-A No. 2007-336778 (Paragraph 0015)
PLT 3: JP-A No. 6-38394 (Paragraph 0010)

Non Patent Literature

NPL 1: Takeno Kazuhiko and Shirota Remi, "Capacity Deterioration Characteristics of Lithium-Ion Batteries for Mobile Phones," NTT DoCoMo Technical Journal, Vol. 13, No. 4 (note that NTT and DoCoMo are registered trademarks).

SUMMARY OF INVENTION

Technical Problem

However, the manufacturer of an electric-powered vehicle is generally different from that of a battery charger. Thus, as in the secondary battery system disclosed in Patent Literature 1, it cannot be said that the charging and discharging information of a secondary battery is always notified from the electric-powered vehicle to the battery charger. In this case, there is a problem in that it is not possible to grasp the deterioration state of the secondary battery during charging.

Moreover, in the charging system disclosed in Patent Literature 2, the battery charger supplies electricity according to a charging instruction from the battery system. That is, since the battery system transmits only the reference value to the battery charger, there is a problem in that it is not possible to grasp the deterioration state of the secondary battery on the charging side.

Moreover, the charging device disclosed in Patent Literature 3 is configured to measure the slope of the charging curve during charging every predetermined intervals of time, compare the measured slopes, and determine whether the charging current will be supplied or stopped. Thus, it is difficult to grasp the state of the secondary battery at respective points in time when charging is performed.

Therefore, an exemplary object of the present invention is to provide a secondary battery state management system, a battery charger, a secondary battery state management method, an electrical characteristics measurement method, and an electrical characteristics measurement program capable of managing the state of the secondary battery during charging.

Solution to Problem

A secondary battery state management system according to the present invention includes: a battery charger that charges a secondary battery; and a storage server that stores electrical characteristic information which is information that indicates electrical characteristics during charging of the secondary battery, in which the battery charger includes electrical characteristic measuring means that measures the electrical characteristics during charging, and in which the storage server includes measurement information storage means that stores the history of the measured electrical characteristic information for each secondary battery, and battery state determining means that compares the electrical characteristic information of the secondary battery being measured by the electrical characteristic measuring means with electrical characteristic information of the same secondary battery stored in the measurement information storage means and determines the state of the secondary battery.

A battery charger according to the present invention is a battery charger that charges a secondary battery, including: electrical characteristic measuring means that measures electrical characteristics during charging of the secondary battery; and transmission means that transmits electrical characteristic information which is information that indicates the electrical characteristics of the secondary battery measured by the electrical characteristic measuring means to a determining device that compares the received electrical characteristic information with the stored history of the electrical characteristic information of the same secondary battery to determine the state of the secondary battery.

A secondary battery state management method according to the present invention includes: allowing a battery charger that charges a secondary battery to measure electrical characteristics during charging; and allowing a storage server that includes a measurement information storage means that stores the history of electrical characteristic information which is information indicating the electrical characteristics for each secondary battery to compare the electrical characteristic information of the secondary battery measured during charging with the electrical characteristic information of the same secondary battery stored in the measurement information storage means to determine the state of the secondary battery.

An electrical characteristics measurement method according to the present invention includes: allowing a battery charger that charges a secondary battery to measure electrical characteristics during charging of the secondary battery; and allowing the battery charger to transmit electrical characteristic information which is information that indicates the measured electrical characteristics of the secondary battery to a determining device that compares the received electrical characteristic information with the stored history of the electrical characteristic information of the same secondary battery to determine the state of the secondary battery.

An electrical characteristics measurement program according to the present invention is an electrical characteristics measurement program that is mounted on a computer that charges a secondary battery, the electrical characteristics measurement program causing the computer to execute: an electrical characteristics measurement process of measuring electrical characteristics during charging of the secondary battery; and a transmission process for transmitting electrical characteristic information which is information that indicates the electrical characteristics of the secondary battery measured in the electrical characteristics measurement process to a determining device that compares the received electrical characteristic information with the stored history of the electrical characteristic information of the same secondary battery to determine the state of the secondary battery.

Advantageous Effects of Invention

According to the present invention, it is possible to manage the state of the secondary battery during charging.

DESCRIPTION OF EMBODIMENTS

Hereinafter, exemplary embodiments of the present invention will be described with reference to the drawings.

First Exemplary Embodiment

Figure 1:
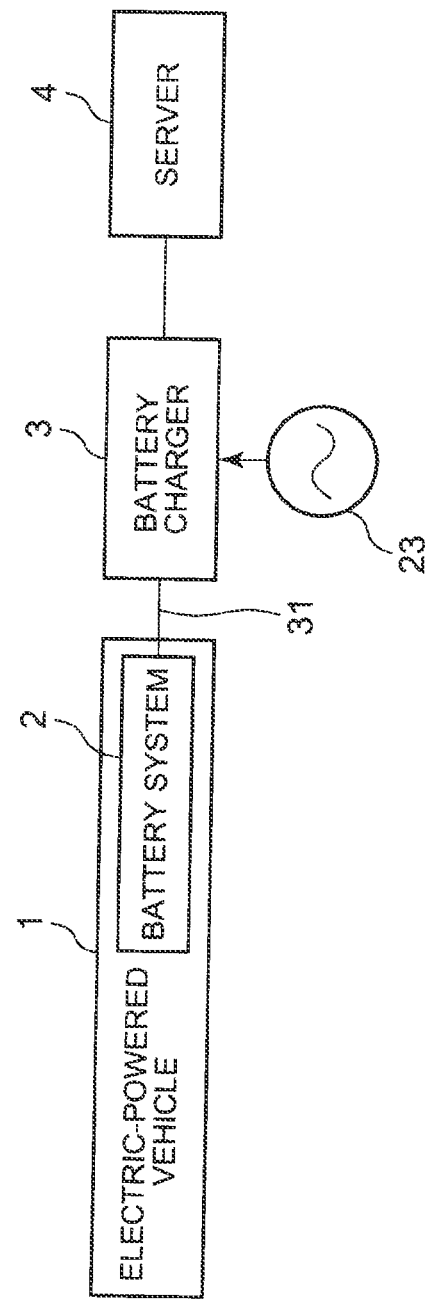
[FIG. 1] It depicts a block diagram illustrating an example of a secondary battery state management system according to a first embodiment of the present invention.

FIG. 1 is a block diagram illustrating an example of a secondary battery state management system according to a first exemplary embodiment of the present invention. The secondary battery state management system according to the present invention includes a battery system 2, a battery charger 3, and a server 4. The battery system 2 is mounted on an electric-powered vehicle 1. Moreover, electricity is supplied to the battery charger 3 from a commercial power supply 23. The battery charger 3 supplies electricity to the battery system 2 via a power feeding line 31. Moreover, the server 4 stores and analyzes the information notified from the battery charger 3.

In the following description, a case where the battery system 2 is mounted on the electric-powered vehicle 1 will be described. The battery system 2 may be mounted on other types of moving vehicles if the moving vehicle can be charged from the battery charger 3.

Figure 2:
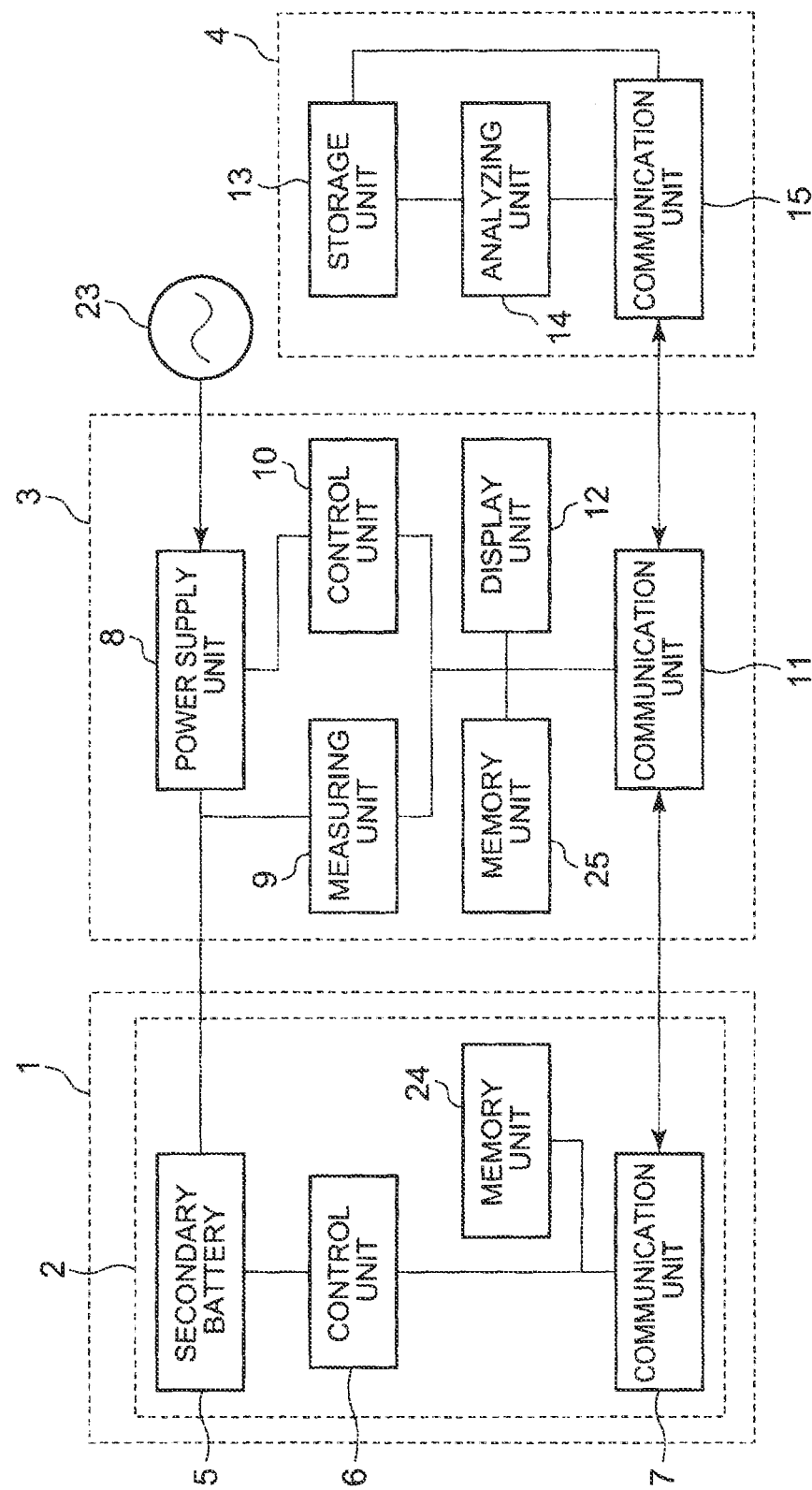
[FIG. 2] It depicts a block diagram illustrating a detailed example of respective constituent components of the secondary battery state management system.

FIG. 2 is a block diagram illustrating a detailed example of respective constituent components of the secondary battery state management system illustrated in FIG. 1. The battery system 2 includes a secondary battery 5, a control unit 6, a communication unit 7, and a memory unit 24.

The secondary battery 5 is a secondary battery that is connected to and charged by the battery charger 3.

The memory unit 24 stores the information notified from the battery charger 3, the information on the battery system 2 itself, and the like. Specifically, the memory unit 24 stores information for identifying the battery charger (hereinafter referred to as a battery charger ID), a protocol version supported by the battery charger, and the like as the information notified from the battery charger 3. Moreover, the memory unit 24 stores information for identifying the battery system (hereinafter referred to as a battery system ID), a protocol version supported by the battery system itself, and the like as the information on the battery system 2 itself. The content stored by the memory unit 24 is not limited to the above content. The memory unit 24 is realized by a memory or the like, for example.

The control unit 6 measures the voltage of the secondary battery 5, an ambient temperature, a current value during charging, or the like, performs control of charging and discharging of the secondary battery 5 according to the value, and generates control information transmitted to the battery charger 3. The control information includes conditions such as a current value necessary for feeding (hereinafter referred to as feeding conditions), in addition to a charging start instruction and a charging stop instruction for the secondary battery 5.

Moreover, when the control unit 6 is connected to the battery charger 3, the control unit transmits the information stored in the memory unit 24 to the battery charger 3. For example, the control unit 6 transmits the battery system ID, the protocol version supported by the battery system 2, and the like stored in the memory unit 24 to the battery charger 3.

The communication unit 7 performs communication with the battery charger 3.

The battery charger 3 includes a power supply unit 8, a measuring unit 9, a control unit 10, a communication unit 11, a display unit 12, and a memory unit 25. When the battery charger 3 is connected to the secondary battery 5, the battery charger 3 charges the connected secondary battery 5.

The memory unit 25 stores the information acquired from the battery system 2 and the server 4, the information on the battery charger 3 itself, and the like. Specifically, the memory unit 25 stores the battery system ID, the protocol version supported by the battery system, and the like as the information acquired from the battery system 2. Moreover, the memory unit 25 stores the information for identifying the battery charger (that is, the battery charger ID), the protocol version supported by the battery charger itself, and the like as the information on the battery charger 3 itself. The content stored in the memory unit 25 is not limited to the above content. The memory unit 25 is realized by a memory or the like, for example.

The power supply unit 8 converts the electricity received from the external commercial power supply 23 into electricity that meets power conditions for charging secondary batteries and supplies the electricity to the secondary battery 5. Specifically, the power supply unit 8 converts an AC current into a DC current and supplies electricity to the secondary battery 5 using the converted DC current.

The measuring unit 9 measures the electrical characteristics during charging of the secondary battery 5. Specifically, the measuring unit 9 measures the electrical characteristics during charging based on measurement conditions that are determined for the battery system 2. The measurement conditions are notified by the server 4 described later. The electrical characteristics measured by the measuring unit 9 include a current value, a voltage value, and the electric energy when the secondary battery is charged.

The information measured by the measuring unit 9 is not limited to the information that indicates the electrical characteristics. The measuring unit 9 may measure an ambient temperature of the battery charger 3 in addition to the electrical characteristics during charging such as a current value, a voltage value, and the electric energy. In the following description, a case where the measuring unit 9 measures the voltage value and the current value at the output terminal of the power supply unit 8 will be described. Moreover, in the following description, the information that indicates the electrical characteristics and the ambient temperature of the battery charger measured by the measuring unit 9 will be referred to as measurement information.

Moreover, the measuring unit 9 identifies a secondary battery, of which the electrical characteristics are to be measured, based on the battery system ID that is notified from the battery system 2 when connected to the secondary battery 5. A method of allowing the measuring unit 9 to identify the secondary battery is not limited to the battery system ID notified from the battery system 2. In the present exemplary embodiment, a case where the measuring unit 9 identifies a secondary battery, of which the electrical characteristics are to be measured, based on the battery system ID notified from the battery system 2 will be described.

The control unit 10 controls the power supply unit 8 so as to match the feeding conditions of the secondary battery 5 based on the control information notified from the battery system 2.

Further, when the battery charger 3 is connected to the battery system 2, the control unit 10 transmits the information stored in the memory unit 25 to the battery system 2. For example, the control unit 10 transmits the battery charger ID, the protocol version supported by the battery charger 3, and the like stored in the memory unit 25 to the battery system 2.

Moreover, the control unit 10 acquires the measurement conditions corresponding to the battery system 2 from the server 4. Specifically, the control unit 10 transmits the battery system ID to the server 4 and receives the measurement conditions that are set for the battery system ID.

Further, the control unit 10 transmits the information that indicates the electrical characteristics during charging to the server 4. The control unit 10 may transmit the measured ambient temperature of the battery charger to the server 4 in addition to the information that indicates the electrical characteristics.

The communication unit 11 performs communication with the battery system 2 and the server 4.

The display unit 12 displays a charging state, a deterioration state, and the like of the secondary battery in accordance with the instruction of the control unit 10. The display unit 12 is realized by a display device such as a display.

The server 4 includes a storage unit 13, an analyzing unit 14, and a communication unit 15.

The storage unit 13 stores the measurement information notified from the battery charger 3. Specifically, the storage unit 13 stores the history of the electrical characteristics information measured by the battery charger 3 with respect to respective secondary batteries.

Moreover, the storage unit 13 stores the measurement conditions corresponding to the battery system 2. The storage unit 13 may store measurement conditions that "measurement is performed at intervals of voltage dV from a reference voltage value V0" for a certain battery system 2, for example. The measurement conditions are stored in advance for the battery system 2. The storage unit 13 is realized by a magnetic disk or the like.

The analyzing unit 14 analyzes the deterioration state of the secondary battery 5 by analyzing and comparing the information notified from the battery charger 3 and the past measurement information stored in the storage unit 13. That is, the analyzing unit 14 compares the electrical characteristics being measured by the measuring unit 9 and the electrical characteristics of the same secondary battery 5, stored in the storage unit 13 and determines the state of the secondary battery 5.

Specifically, the analyzing unit 14 extracts the history of the past measurement information stored in the storage unit 13 based on the battery system ID (specifically, the battery system ID notified from the battery system 2 to the battery charger 3) notified from the battery charger 3. Moreover, the analyzing unit 14 determines the state of the secondary battery 5 by comparing the measurement information measured by the battery charger 3 with the history in which the voltage value and the current value are identical to those of the measurement information. A method of allowing the analyzing unit 14 to determining the state of the secondary battery 5 will be described later.

Moreover, the analyzing unit 14 transmits the measurement conditions to the battery charger 3. Specifically, upon receiving the request for the battery system ID and the measurement conditions from the battery charger 3, the analyzing unit 14 extracts the measurement conditions from the storage unit 13 based on the battery system ID as a key and sends the extracted measurement conditions to the battery charger 3.

In the above description, a case where the storage unit 13 stores the measurement conditions corresponding to the battery system, and the analyzing unit 14 extracts the measurement conditions corresponding to the battery system ID that is received from the battery charger 3 has been described. However, the storage unit 13 may store the measurement conditions for each manufacturer and each vehicle type of the electric-powered vehicles rather than for each battery system. For example, when the battery charger 3 receives information (for example, a manufacturer ID and a vehicle type ID) that can identify the manufacturer and the vehicle type of an electric-powered vehicle from the battery system 2, the analyzing unit 14 may receive these items of identification information from the battery charger 3 and extract the corresponding measurement conditions.

Moreover, information in which the manufacturer and the vehicle type of the electric-powered vehicle are associated with the battery system ID may be stored in advance in the storage unit 13. In this case, when the server 4 receives the battery system ID from the battery charger 3, the analyzing unit 14 may extract the manufacturer and the vehicle type of the electric-powered vehicle corresponding to the battery system ID from the storage unit 13 and then extract the measurement conditions corresponding to the extracted manufacturer and vehicle type of the electric-powered vehicle from the storage unit 13.

The communication unit 15 performs communication with the battery charger 3.

The measuring unit 9 and the control unit 10 are realized by the CPU of a computer that operates according to a program (an electrical characteristics measurement program). For example, the program may be stored in the memory unit 25 of the battery charger 3, and the CPU may read the program and operate as the measuring unit 9 and the control unit 10 according to the program. Moreover, the measuring unit 9 and the control unit 10 may be individually realized by dedicated hardware.

Figure 3:
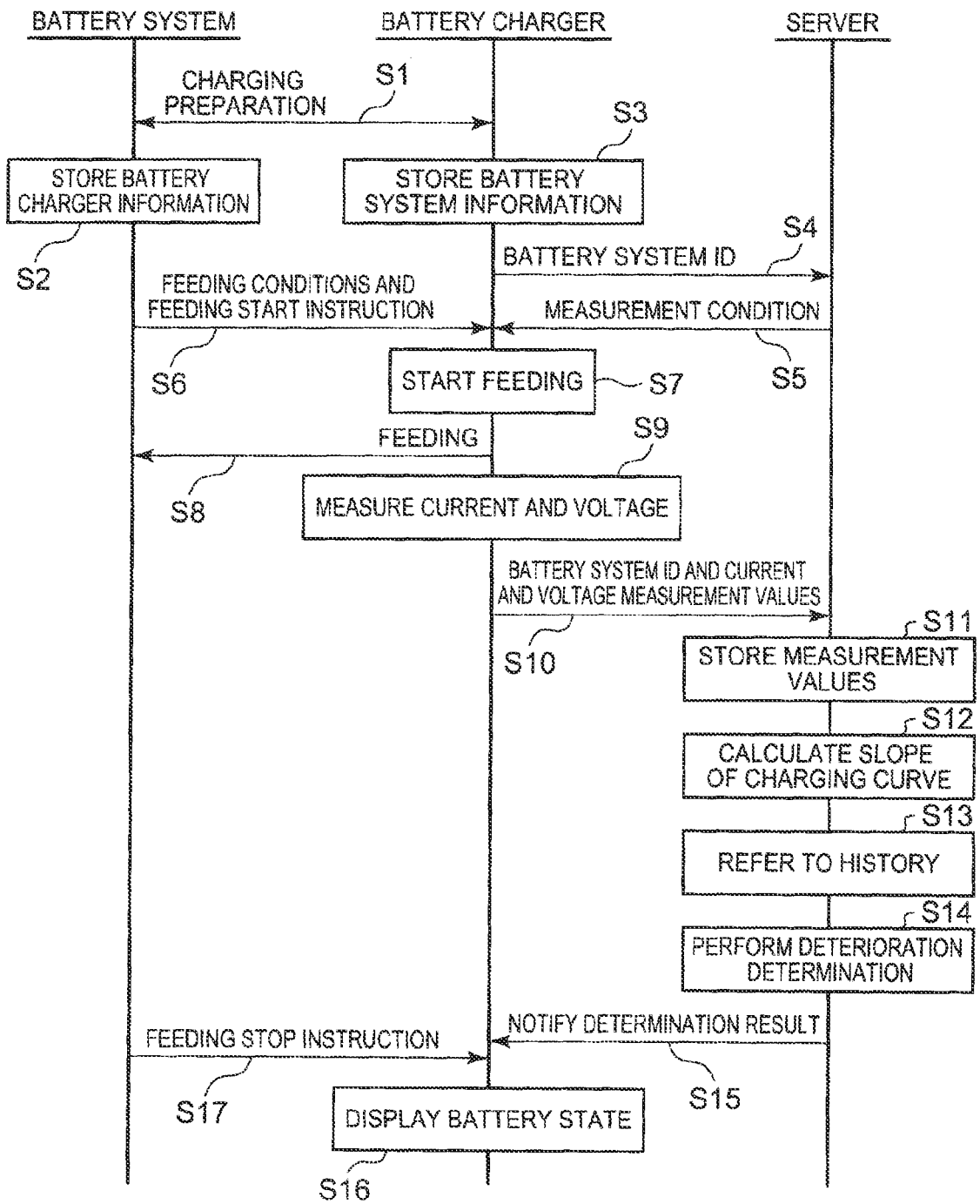
[FIG. 3] It depicts a sequence diagram illustrating an example of the operation according to the first embodiment.

Next, the operation of the first exemplary embodiment will be described. FIG. 3 is a sequence diagram illustrating an example of the process performed between the battery system 2, the battery charger 3, and the server 4.

When the battery charger 3 is connected to the battery system 2, a process of exchanging the battery system ID and the battery charger ID for identifying the respective devices, a process of exchanging the protocol versions supported by the respective devices in order to determine an operating level, and the like are performed between the control units of the battery system 2 and the battery charger 3 as a charging preparation process (step S1). Specifically, using the connection of the battery charger 3 to the battery system 2 as a trigger, the control unit 10 transmits the battery charger ID stored in the memory unit 25 to the battery system 2, and the control unit 6 transmits the battery system ID stored in the memory unit 24 to the battery charger 3. The control unit 6 of the battery system 2 and the control unit 10 of the battery charger 3 store the exchanged information in the memory unit 24 and the memory unit 25, respectively (steps S2 and S3).

When the charging preparation process is completed, the battery charger 3 acquires the measurement conditions from the server 4 (specifically, the storage unit 13) using the battery system ID acquired in the charging preparation process as a key (steps S4 and S5). Moreover, the control unit 6 of the battery system 2 transmits feeding conditions and a feeding start instruction to the control unit 10 of the battery charger 3 (step S6). When the battery charger 3 receives these items of information, the control unit 10 of the battery charger 3 controls the power supply unit 8 based on requested feeding conditions and start supply of electricity (steps S7 and S8).

When the power supply unit 8 of the battery charger 3 starts supply of electricity, the measuring unit 9 measures a value of the voltage between power feeding lines and a value of the current that flows through the power feeding line in a discrete manner according to the measurement conditions acquired from the server 4 (step S9). For example, when the measurement conditions that "measurement is performed at intervals of voltage dV from a reference voltage value V0" are set, the measuring unit 9 measures the current value when a voltage is applied at intervals of voltage dV from the reference voltage value V0 according to the measurement conditions. The control unit 10 of the battery charger 3 notifies the current value and the voltage value measured by the measuring unit 9 to the server 4 together with the battery system ID, the ambient temperature of the battery charger, the battery charger ID, and the measurement time (step S10). The control unit 10 of the battery charger 3 may notify information other than the above to the server 4.

When the server 4 receives the notification from the battery charger 3, the analyzing unit 14 stores the received information in the storage unit 13 (step S11). The analyzing unit 14 receives at least one item of information among the value of the voltage between the power feeding lines 31 and the value of the current that flows through the power feeding line 31, the value of the voltage between the power feeding lines 31 and the electric energy supplied from the power feeding line 31 to the secondary battery, and information (for example, impedance) calculated from these items of information from the battery charger 3 along with the battery system ID of the secondary battery, for example, and stores the received information in the storage unit 13. The stored information may include the date and time of charging and information on the battery charger.

Moreover, the analyzing unit 14 analyzes the state of the secondary battery based on the measurement information stored in the storage unit 13. Hereinafter, a method of analyzing the deterioration state of a secondary battery will be described in detail.

Figure 4:
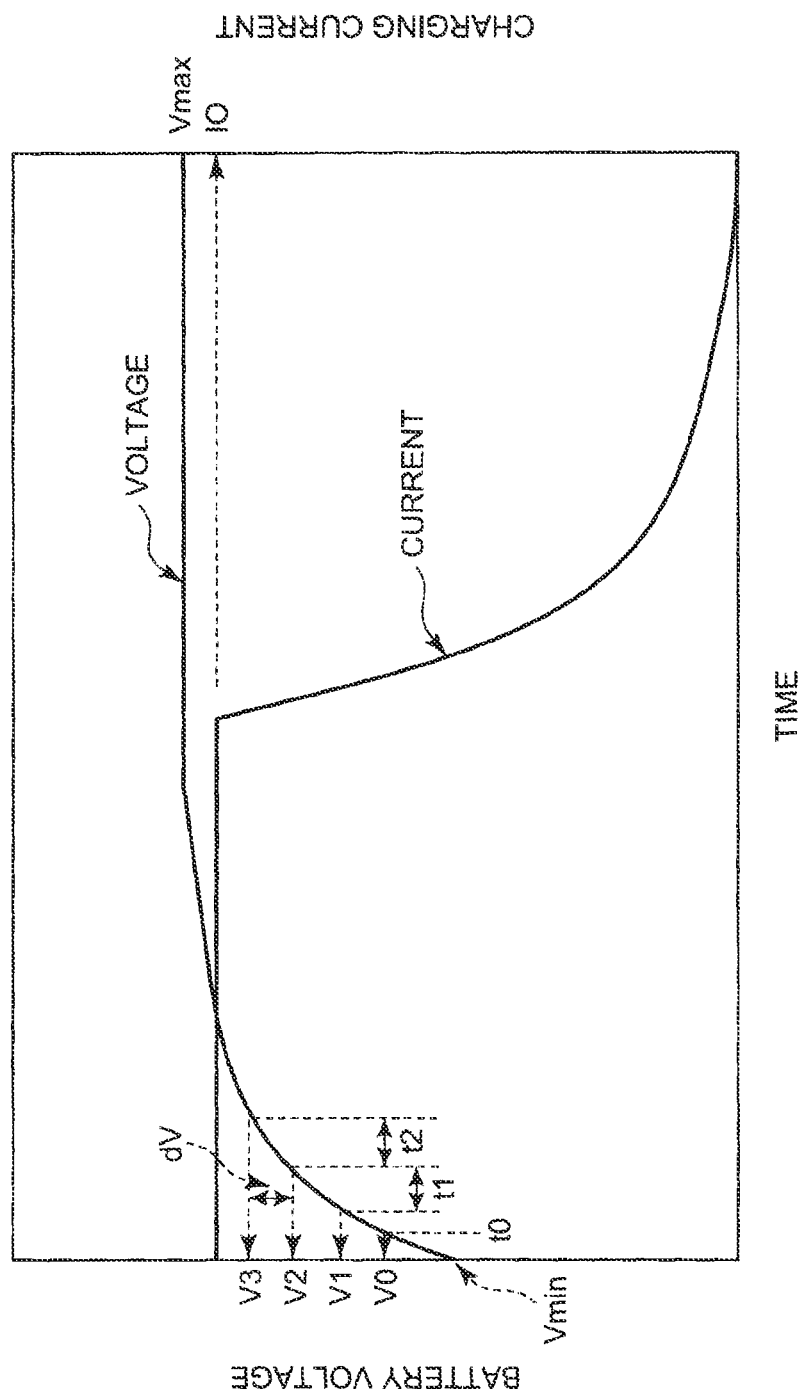
[FIG. 4] It depicts an explanatory diagram illustrating an example of the charging characteristics of a lithium-ion battery.

FIG. 4 is an explanatory diagram illustrating an example of the charging characteristics of a lithium-ion battery. The explanatory diagram illustrated in FIG. 4 illustrates a change of a voltage value and a current value when a lithium-ion battery is charged according to a method called a constant-current/constant-voltage charging mode. This mode is characterized in that charging is first performed with a constant current (I0), and charging is performed with a constant voltage when the voltage value reaches a certain value (Vmax). In FIG. 4, "Vmin" indicates a battery voltage when measurement starts, and "Vmax" indicates a voltage value when charging is performed with a constant voltage. Moreover, "t0" indicates a period required for changing the battery voltage from Vmin to V0, "t1" indicates a period required for changing the battery voltage from V1 to V2, and "t2" indicates a period required for changing the battery voltage from V2 to V3.

When a secondary battery deteriorates, the amount of change per single time of the battery voltage during the constant-current charging is different even if the conditions such as a voltage value, a current value, and a temperature are the same. Thus, the analyzing unit 14 of the server 4 calculates the slope values (dV/t0, dV/t1, dV/t2, and the like) at a plurality of points (for example, battery voltage values V0, V1, V2, V3, and the like) on the battery voltage curve during the constant-current charging (step S12) and stores the slope values in the storage unit 13. Moreover, the analyzing unit 14 refers to slope values of the battery voltage curve under the same conditions (for example, when the voltage value, the current value, and the temperature are the same) from the past measurement history of the same battery system ID (step S13) and compares both slope values to perform deterioration determination (step S14).

Moreover, "Vmin" and "Vmax" in the battery voltage curve illustrated in FIG. 4 have different values depending on the configuration of the battery system. Thus, a person may determine the points (for example, the battery voltage values V1, V2, V3, and the like), at which the slope values are calculated, based on the battery voltage curve derived by the analyzing unit 14, and the points may be stored in the storage unit 13 of the server 4.

Moreover, the analyzing unit 14 may use the ambient temperature of the battery charger 3 received from the battery charger 3 as the deterioration determination conditions. In general, a battery charging method is changed depending on the surface temperature of a battery. Thus, even if it is not possible to directly measure the temperature of a secondary battery in a vehicle, the ambient temperature of the battery charger 3 may be measured, and the measured temperature maybe regarded as the surface temperature of the secondary battery. Therefore, by assuming that the charging method is the same if the ambient temperature of the battery charger 3 is the same, the past measurement information including the temperature as measurement conditions may be compared. By performing such comparison, it is possible to improve the estimation accuracy of the deterioration determination.

Moreover, when the control unit 6 of the battery system 2 notifies the surface temperature of the secondary battery 5 to the battery charger 3, the battery charger 3 may transmit the surface temperature of the secondary battery to the server 4. In this case, the analyzing unit 14 can use the surface temperature of the secondary battery 5 as the deterioration determination conditions.

When the deterioration determination is performed, the analyzing unit 14 of the server 4 notifies the determination result to the battery charger 3 (step S15). The control unit 10 of the battery charger 3 displays a message for informing the state of the battery on the display unit 12 based on the received deterioration determination (step S16). After that, when the voltage value of the secondary battery 5 reaches a predetermined value, the control unit 6 outputs a feeding stop instruction to the battery charger 3 (step S17).

As described above, according to the present exemplary embodiment, the measuring unit 9 of the battery charger 3 measures the electrical characteristics during charging of the secondary battery 5. Moreover, the analyzing unit 14 of the server 4 compares the electrical characteristics being measured by the measuring unit 9 with the electrical characteristics of the same secondary battery 5, stored in the storage unit 13 and determines the state of the secondary battery 5. Specifically, the measuring unit 9 included in the battery charger 3 measures the voltage value and the current value during charging of the secondary battery 5 connected to the battery charger 3. Moreover, the analyzing unit 14 compares the measurement values with the past measurement values stored in correlation with the identification information (for example, the battery system ID) of each of the individual secondary batteries. Therefore, even when information such as the charging characteristics of the secondary battery 5 is not obtained from the electric-powered vehicle, it is possible to manage the state of the secondary battery during charging.

Moreover, according to the present exemplary embodiment, the storage unit 13 stores the measurement information such as the current value and the voltage value that are notified from the battery charger 3. Thus, in the server 4, it is possible to depict a charging characteristics curve corresponding to the battery system. That is, it is possible to visualize the charging characteristics curve corresponding to the battery system on the side of the server 4.

Second Exemplary Embodiment

Next, a second exemplary embodiment of the present invention will be described. The configuration of the second exemplary embodiment is the same as the configuration of the first exemplary embodiment illustrated in FIG. 2. However, in the present exemplary embodiment, the information processed by the measuring unit 9 of the battery charger 3 and the analyzing unit 14 of the server 4 is different from that of the first exemplary embodiment.

Specifically, in the first exemplary embodiment, a method in which the measuring unit 9 of the battery charger 3 measures the current value and the voltage value during charging, and the analyzing unit 14 of the server 4 estimates the deterioration state of a secondary battery from the slope of a voltage variation curve has been described. On the other hand, the second exemplary embodiment is different from the first exemplary embodiment in that the measuring unit 9 of the battery charger 3 measures the voltage value and the electric energy during charging, and the analyzing unit 14 of the server 4 estimates the deterioration state of a secondary battery from the electric energy of the secondary battery under the same voltage variation.

Figure 5:
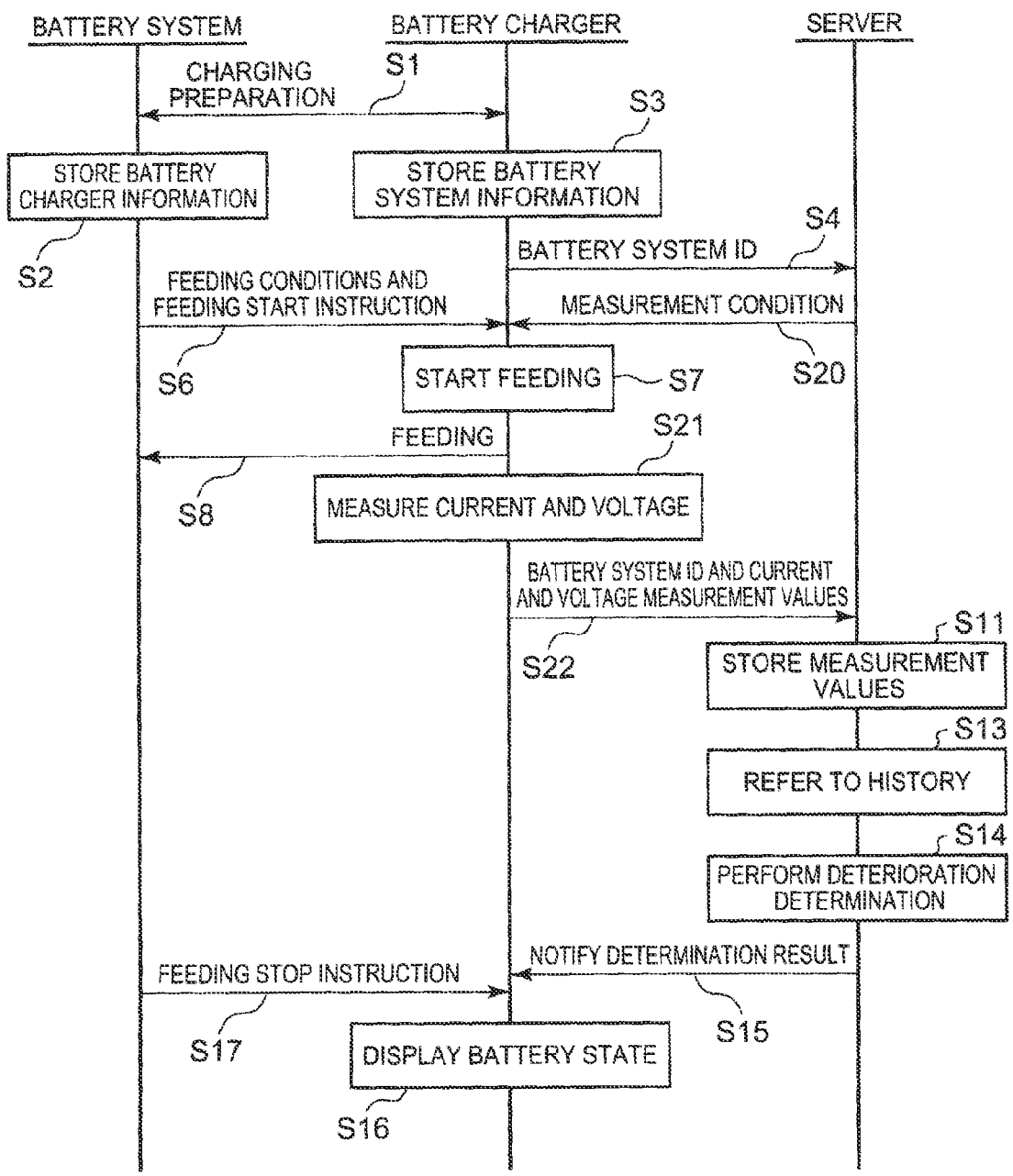
[FIG. 5] It depicts a sequence diagram illustrating an example of the operation according to a second embodiment.

Hereinafter, the operation of the second exemplary embodiment will be described. FIG. 5 is a sequence diagram illustrating an example of the process performed between the battery system 2, the battery charger 3, and the server 4.

When the battery charger 3 is connected to the battery system 2, a process of exchanging the battery system ID and the battery charger ID for identifying the respective devices, a process of exchanging the protocol versions supported by the respective devices in order to determine an operating level, and the like are performed between the control units of the battery system 2 and the battery charger 3 (specifically, between the control unit 6 of the battery system 2 and the control unit 10 of the battery charger 3) as a charging preparation process (step S1). The content of the charging preparation process is the same as that of the first exemplary embodiment. The control unit 6 of the battery system 2 and the control unit 10 of the battery charger 3 store the exchanged information in the memory unit 24 and the memory unit 25, respectively (steps S2 and S3).

Subsequently, the battery charger 3 notifies the battery system ID acquired from the battery system 2 to the server 4 (step S4). The analyzing unit 14 of the server 4 acquires the measurement conditions stored in advance in the storage unit 13 and notifies the measurement conditions to the battery charger 3 (step S20). In the following description, the measurement conditions are also referred to as measurement parameters.

For example, the storage unit 13 may store a voltage value Vs at the start of electricity measurement, a voltage value Ve at the end of electricity measurement, and voltage values V0 to Vn (hereinafter these voltage values will be referred to as intermediate points) between Vs and Ve as the measurement parameters. The number n of intermediate points is an arbitrary integer of 0 or more. However, the content of the measurement parameters is not limited to the above.

When the charging preparation process is completed, the control unit 6 of the battery system 2 notifies the feeding conditions and a feeding start instruction to the control unit 10 of the battery charger 3 (step S6). When the battery charger 3 receives these items of information, the control unit 10 of the battery charger 3 controls the power supply unit 8 based on requested feeding conditions and start supply of electricity (steps S7 and S8).

When the power supply unit 8 of the battery charger 3 starts supply of electricity, the measuring unit 9 measures the value of the voltage between power feeding lines. Moreover, when the voltage value reaches Vs, the measuring unit 9 starts measurement of the electric energy supplied to the secondary battery (step S21). The measuring unit 9 may measure the electric energy by calculating the product of a voltage value, a current value, and a measurement time, for example. Hereinafter, the electric energy calculated in this manner is also referred to as an integral electricity value. The measuring unit 9 calculates the integral electricity value of each of the intervals of the intermediate points (that is, V0 to Vn) until the voltage value reaches Ve, and ends the measurement of the electric energy supplied to the secondary battery when the voltage value reaches Ve.

The control unit 10 of the battery charger 3 notifies the integral electricity value measured by the measuring unit 9 to the server 4 along with the voltage value at the start of the measurement, the voltage value at the end of the measurement, the voltage values at the intermediate points, the battery system ID, the ambient temperature of the battery charger, the battery charger ID, and the measurement time (step S22). The control unit 10 of the battery charger 3 may notify information other than the above to the server 4.

When the server 4 receives the notification from the battery charger 3, the analyzing unit 14 stores the received information in the storage unit 13 (step S11). Moreover, the analyzing unit 14 refers to the measurement information stored in the storage unit 13 (step S13) and performs analysis (that is, deterioration determination) on the state of the secondary battery (step S14). Hereinafter, a method of analyzing the deterioration state of a secondary battery will be described in detail.

A secondary battery has such characteristics that when the secondary battery deteriorates, the amount of actually charged electricity decreases with a change (that is, an increase of apparent power capacity) of the voltage value during charging. Thus, the analyzing unit 14 of the server 4 compares the electric energy supplied to the secondary battery with a predetermined change of the voltage value (for example, a change in which the voltage value changes from a first voltage value to a second voltage value), and performs deterioration determination based on whether the electric energy tends to decrease or not. That is, when the integral electricity value decreases, the analyzing unit 14 determines that the secondary battery deteriorates.

The voltage values Vs, Ve, and V0 to Vn used when measuring the integral electricity value have different values depending on the configuration of the battery system. Therefore, a person may determine the voltage values Vs, Ve, and V0 to Vn based on a voltage variation range stored in the storage unit 13.

When the deterioration determination is performed, the analyzing unit 14 of the server 4 notifies the determination result to the battery charger 3 (step S15). The control unit 10 of the battery charger 3 displays a message for informing the state of the battery on the display unit 12 based on the received deterioration determination (step S16). After that, when the voltage value of the secondary battery 5 reaches a predetermined value, the control unit 6 outputs a feeding stop instruction to the battery charger 3 (step S17).

As described above, in the present exemplary embodiment, the analyzing unit 14 of the server 4 compares the voltage value and the electric energy being measured by the measuring unit 9 with the voltage value and the electric energy of the same secondary battery 5, stored in the storage unit 13 and determines the state of the secondary battery 5. By doing so, it is also possible to manage the state of the secondary battery during charging.

In the second exemplary embodiment, a case where the integral electric energy is measured within the battery charger 3 (that is, by the control unit 9) has been described. However, the invention is not limited to the case where the measurement of the integral electric energy is performed by the control unit 9. Similarly to the first exemplary embodiment, the control unit 9 of the battery charger 3 may measure the current value and the voltage value at a short measurement interval and sends the measurement results to the server 4, and the analyzing unit 14 of the server 4 may calculate the integral electric energy based on the received measurement results.

However, in order to decrease an error in the electric energy that is calculated based on the voltage value and the current value, it is necessary to measure the values at short intervals. That is, when the electric energy is calculated on the side of the server 4, the measuring unit 9 needs to notify the voltage value and the current value measured at short intervals to the server 4. On the other hand, when the electric energy is measured on the side of the battery charger 3, the voltage value and the current value used for calculating the electric energy do not need to be transmitted to the side of the server 4. Thus, since the amount of information transmitted can be decreased at the same measurement intervals of the voltage value and the current value, it is possible to obtain an advantage that a network load between the battery charger 3 and the server 4 decreases.

Third Exemplary Embodiment

Figure 6:
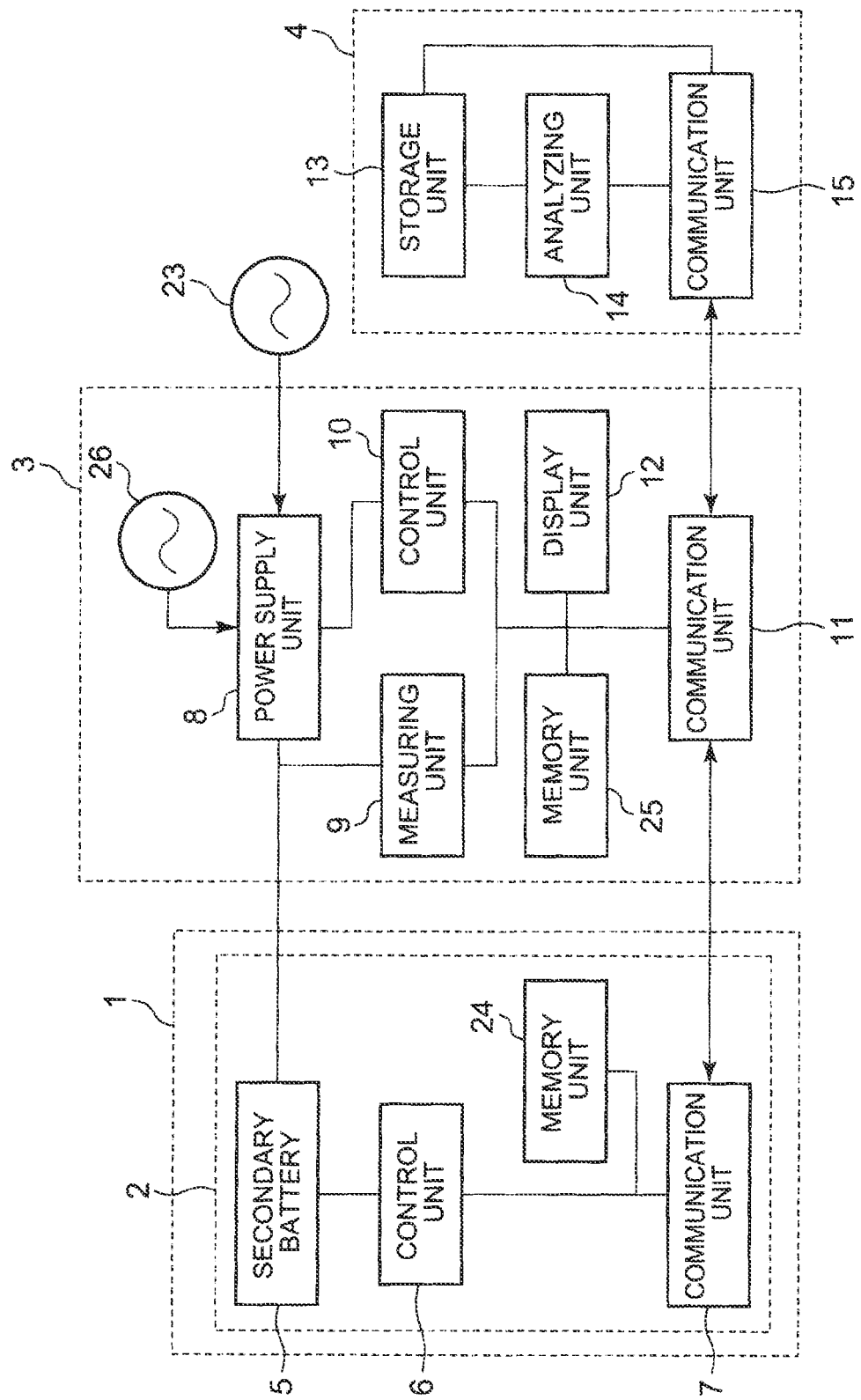
[FIG. 6] It depicts a block diagram illustrating a detailed example of respective constituent components of a secondary battery state management system according to a third embodiment of the present invention.

Next, a third exemplary embodiment of the present invention will be described. FIG. 6 is a block diagram illustrating a detailed example of respective constituent components of a secondary battery state management system according to the third exemplary embodiment of the present invention. The same configurations as those of the first and second exemplary embodiments will be denoted by the same reference numerals of FIG. 2, and description thereof will not be provided. The battery charger 3 of the present exemplary embodiment is different from the battery charger 3 of the first exemplary embodiment in that the battery charger 3 further includes an AC impedance measurement signal source (hereinafter, a signal source) 26.

The signal source 26 superimposes an AC signal for AC impedance measurement on power feeding lines. The superimposed AC signal is determined in advance depending on the configuration of the battery system 2.

Moreover, in the present exemplary embodiment, the information processed by the measuring unit 9 of the battery charger 3 and the analyzing unit 14 of the server 4 is different from that of the first and second exemplary embodiments. Specifically, in the first exemplary embodiment, the measuring unit 9 of the battery charger 3 measures the current value and the voltage value during charging, and the analyzing unit 14 of the server 4 estimates the deterioration state of a secondary battery from the slope of a voltage variation curve. Moreover, in the second exemplary embodiment, the measuring unit 9 of the battery charger 3 measures the voltage value and the electric energy during charging, and the analyzing unit 14 of the server 4 estimates the deterioration state of a secondary battery from the electric energy of the secondary battery under the same voltage variation.

On the other hand, the third exemplary embodiment is different from the first and second exemplary embodiments in that the signal source 26 superimposes an AC signal on the power feeding lines 31 through which power is supplied from the battery charger 3 to the secondary battery 5, and the measuring unit 9 of the battery charger 3 measures an AC impedance of the AC signal. Moreover, the third exemplary embodiment is different from the first and second exemplary embodiments in that the analyzing unit 14 of the server 4 estimates the deterioration state of the secondary battery based on a change from the past AC impedance measurement value.

Figure 7:
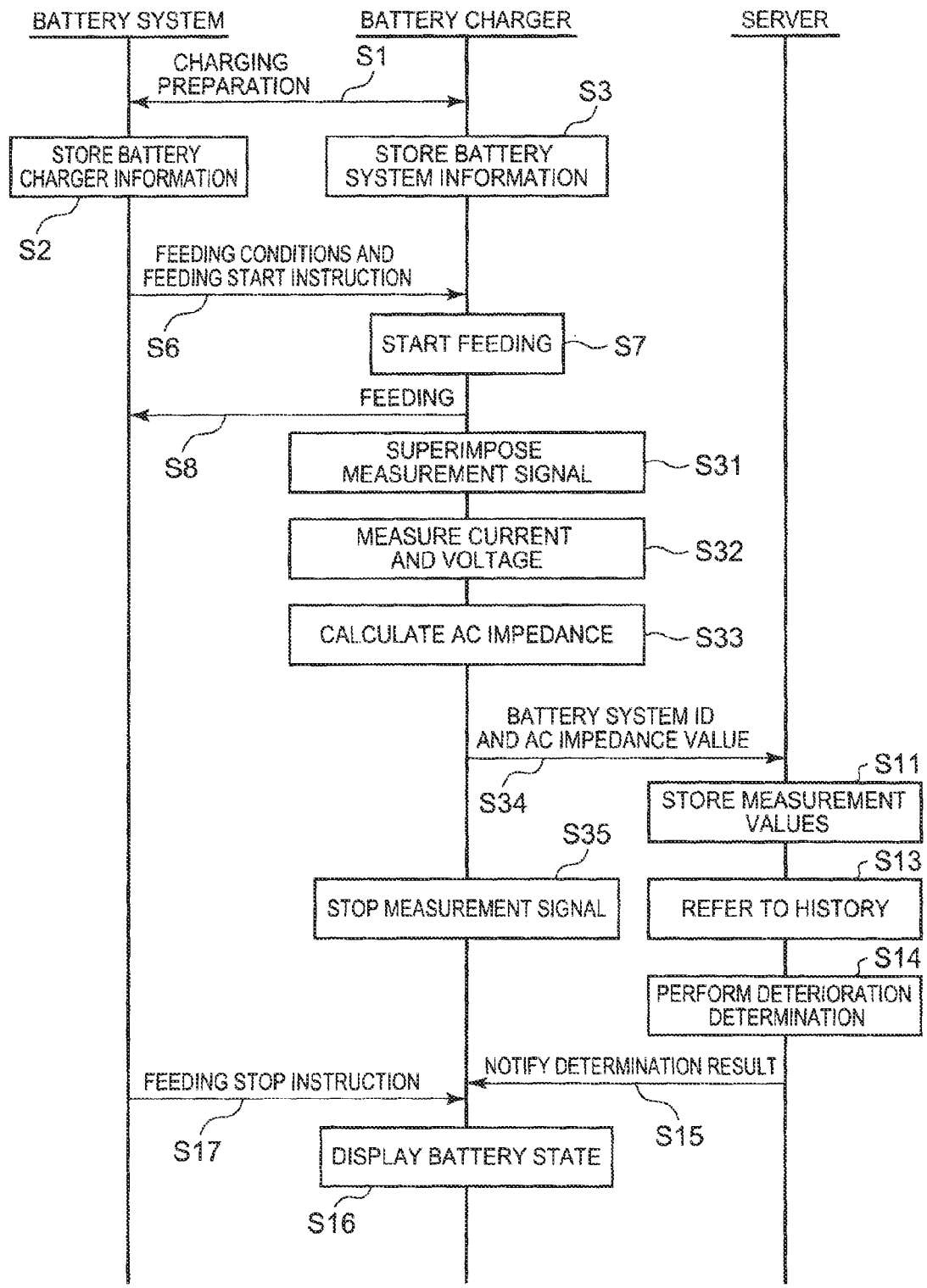
[FIG. 7] It depicts a sequence diagram illustrating an example of the operation according to the second embodiment.

Hereinafter, the operation of the third exemplary embodiment will be described. FIG. 7 is a sequence diagram illustrating an example of the process performed between the battery system 2, the battery charger 3, and the server 4.

When the battery charger 3 is connected to the battery system 2, a process of exchanging the battery system ID and the battery charger ID for identifying the respective devices, a process of exchanging the protocol versions supported by the respective devices in order to determine an operating level, and the like are performed between the control units (specifically, between the control unit 6 of the battery system 2 and the control unit 10 of the battery charger 3) of the battery system 2 and the battery charger 3 as a charging preparation process (step S1). The control unit 6 of the battery system 2 and the control unit 10 of the battery charger 3 store the exchanged information in the memory unit 24 and the memory unit 25, respectively (steps S2 and S3).

When the charging preparation process is completed, the control unit 6 of the battery system 2 notifies the feeding conditions and a feeding start instruction to the control unit 10 of the battery charger 3 (step S6). When the battery charger 3 receives these items of information, the control unit 10 of the battery charger 3 controls the power supply unit 8 based on requested feeding conditions and starts supply of electricity (steps S7 and S8).

When the power supply unit 8 of the battery charger 3 starts supply of electricity, the control unit 10 of the battery charger 3 instructs the power supply unit 8 to superimpose a signal from an AC impedance measurement signal source 26 on the power feeding line 31. Moreover, the power supply unit 8 outputs the signal from the signal source 26 to the power feeding line 31 (step S31). The signal source 26 outputs an AC signal of which frequency is 1 kHz and the current amplitude is 5 A, for example. However, the AC signal output by the signal source 26 is not limited to the above-described contents.

The control unit 10 instructs the power supply unit 8 to superimpose the signal from the signal source 26. Moreover, the control unit 10 outputs an instruction to measure an effective voltage value and an effective current value to the measuring unit 9 (step S32) and outputs an instruction to calculate an impedance (hereinafter also referred to as an impedance |Z|) based on these values (step S33).

When the impedance |Z| is calculated, the control unit 10 instructs the power supply unit 8 to stop superimposing the signal from the signal source 26, and the power supply unit 8 stops superimposing the measurement signal from the signal source 26 (step S35).

Moreover, the control unit 10 notifies the calculated impedance |Z| to the server 4 along with the battery system ID, the ambient temperature of the battery charger, the battery charger ID, and the measurement time (step S34). The control unit 10 may notify information other than the above to the server 4.

When the server 4 receives the notification from the battery charger 3, the analyzing unit 14 stores the received information in the storage unit 13 (step S11). Moreover, the analyzing unit 14 refers to the measurement information stored in the storage unit 13 (step S13) and performs analysis (that is, deterioration determination) on the state of the secondary battery (step S14). Hereinafter, a method of analyzing the deterioration state of a secondary battery will be described in detail.

A secondary battery has such characteristics that when the secondary battery deteriorates, an AC impedance increases. Thus, the analyzing unit 14 of the server 4 compares the history information of the AC impedance values of the same battery system ID and performs deterioration determination based on whether the AC impedance value tends to increase or not. That is, when the calculated impedance increases, the analyzing unit 14 determines that the secondary battery deteriorates.

When the deterioration determination is performed, the analyzing unit 14 of the server 4 notifies the determination result to the battery charger 3 (step S15). The control unit 10 of the battery charger 3 displays a message for informing the battery state on the display unit 12 based on the received deterioration determination (step S16). After that, when the voltage value of the secondary battery 5 reaches a predetermined value, the control unit 6 outputs a feeding stop instruction to the battery charger 3 (step S17).

As described above, according to the present exemplary embodiment, the measuring unit 9 of the battery charger 3 calculates the AC impedance based on an AC voltage between the power feeding lines 31 and the AC signal when the AC signal output from the signal source 26 is superimposed on the power feeding lines 31. Moreover, the analyzing unit 14 of the server 4 compares the calculated AC impedance with the impedance of the same secondary battery 5 stored in the storage unit 13, and determines the state of the secondary battery 5. By doing so, it is also possible to manage the state of the secondary battery during charging.

Fourth Exemplary Embodiment

In the first to third exemplary embodiments, a case where the battery system is identified using the battery system ID notified from the battery system 2 has been described. In a fourth exemplary embodiment, it is different from the first to third exemplary embodiments in that the number on a number plate attached to the electric-powered vehicle 1 on which the battery system 2 is mounted is used as the identification information (ID) of the battery system.

Figure 8:
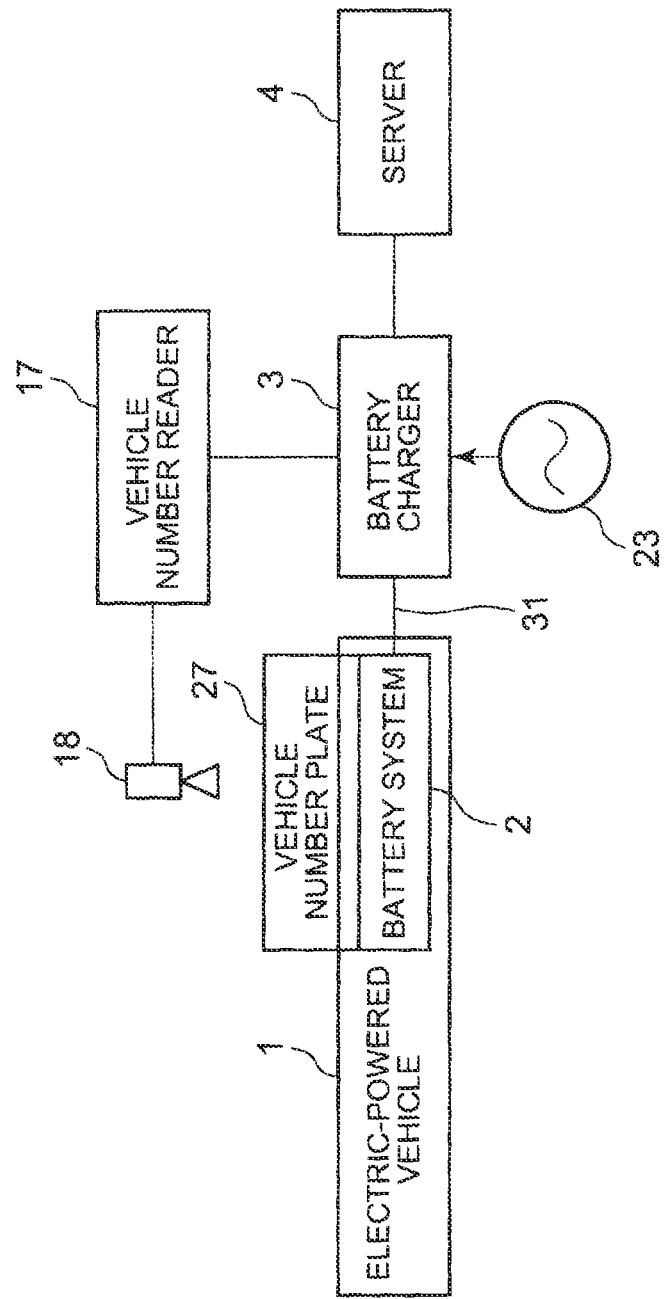
[FIG. 8] It depicts a block diagram illustrating an example of a secondary battery state management system according to a fourth embodiment of the present invention.

FIG. 8 is a block diagram illustrating an example of a secondary battery state management system according to the fourth exemplary embodiment. The secondary battery state management system of the present exemplary embodiment includes the battery system 2, the battery charger 3, the server 4, a vehicle number reader 17, and a camera 18. Moreover, the electric-powered vehicle 1 on which the battery system 2 is mounted is provided with an electric-powered vehicle plate 27. The electric-powered vehicle plate 27 is an identification number of a vehicle, and for example, is an automobile registration number plate or a vehicle number plate (number plate) for identifying a vehicle. Moreover, the camera 18 is connected to the vehicle number reader 17, and the vehicle number reader 17 is connected to the battery charger 3. The other configurations are the same as those of the first to third exemplary embodiments.

The camera 18 photographs the electric-powered vehicle plate 27 to obtain an image. Moreover, the vehicle number reader 17 reads the image photographed by the camera 18 to recognize a vehicle number. Since a method of recognizing a vehicle number from a photographed image is widely known, description thereof will not be provided herein.

As above, the fourth exemplary embodiment is different from the first exemplary embodiment in that the battery charger 3, the camera 18 that photographs the electric-powered vehicle plate 27, and the vehicle number reader 17 that recognizes a vehicle number from the photographed image are connected, and the vehicle number is used instead of the battery system ID.

Next, the operation of the fourth exemplary embodiment will be described. In the following description, a case where rather than acquiring the battery system ID from the battery system 2 as in the first exemplary embodiment, the information (hereinafter referred to as vehicle number) for identifying a vehicle is acquired from the electric-powered vehicle plate 27 will be described.

Figure 9:
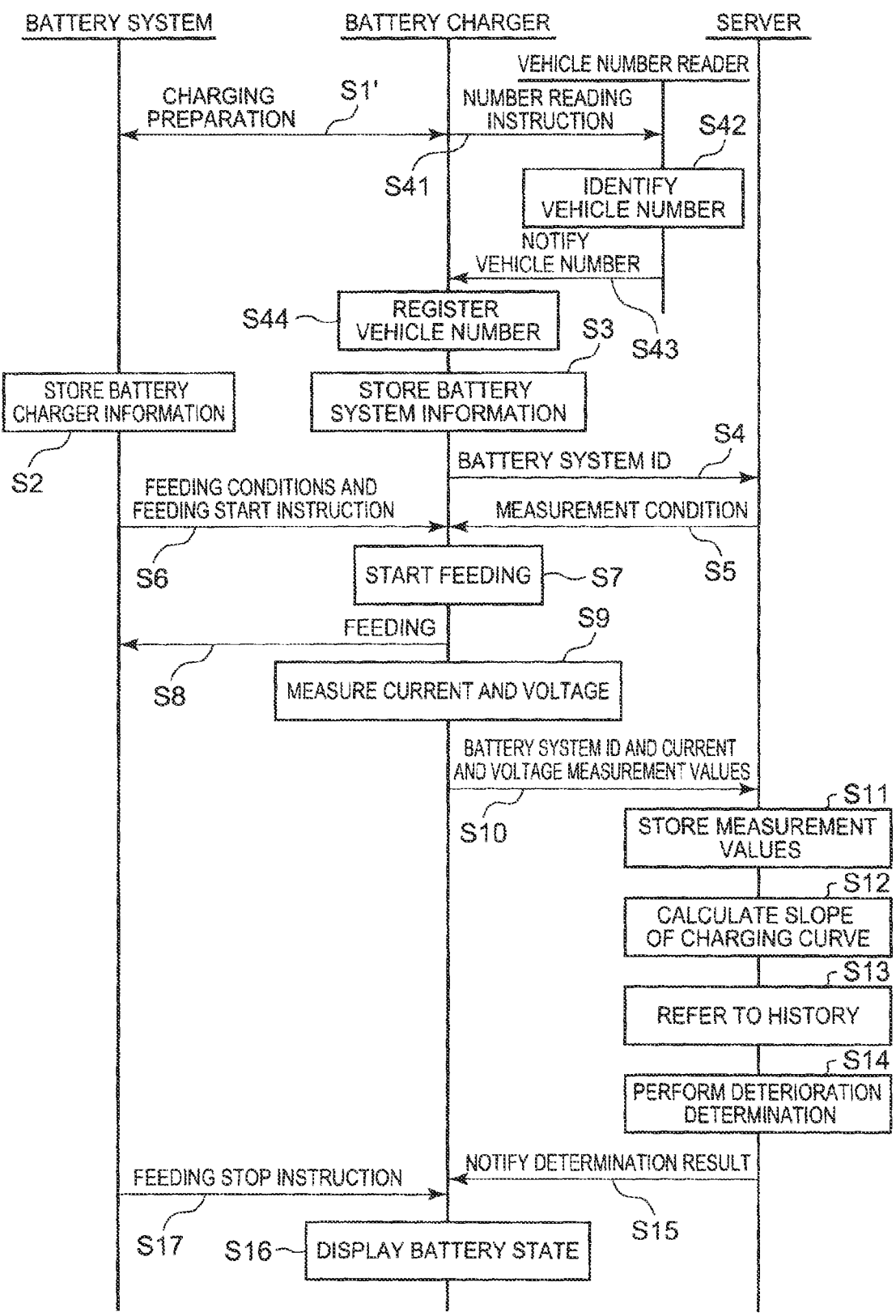
[FIG. 9] It depicts a sequence diagram illustrating an example of an operation of acquiring a vehicle number from an electric-powered vehicle number plate 27.

FIG. 9 is a sequence diagram illustrating an example of the operation of acquiring the vehicle number from the electric-powered vehicle plate 27 instead of the battery system ID.

When the battery charger 3 is connected to the battery system 2, a charging preparation process is executed between the battery system 2 and the battery charger 3 in a manner similar to the first to third exemplary embodiments (step S1'). This process is different from the process of step S1 of FIG. 3 in that the battery system ID is not notified to the battery charger 3.

Moreover, in parallel with the charging preparation process, the control unit 10 of the battery charger 3 instructs the vehicle number reader 17 to read the number on the electric-powered vehicle plate 27 (step S41). The vehicle number reader 17 recognizes the vehicle number from the image photographed by the camera 18 (step S42) and notifies the recognized vehicle number to the battery charger 3 (step S43). Upon receiving the vehicle number, the control unit 10 of the battery charger 3 stores the value in the memory unit 25 (step S44).

The processes of performing deterioration determination based on the measured values are the same as the processes of steps S2 to S17 illustrated in FIG. 3. It should be noted that in the respective processes, the vehicle number is used instead of the battery system ID.

In the above description, a case where the process of acquiring the vehicle number from the electric-powered vehicle plate 27 and the process of using the vehicle number instead of the battery system ID are performed in parallel with the charging preparation process of the first exemplary embodiment has been described. These processes can be applied to the second and third exemplary embodiments as well as the first exemplary embodiment.

As described above, according to the present exemplary embodiment, when the battery charger 3 is connected to the secondary battery, the measuring unit 9 of the battery charger 3 receives the identification information indicated by the vehicle number plate 27 of the electric-powered vehicle 1, read by the vehicle number reader 17 and identifies a secondary battery, of which the electrical characteristics are to be measured, based on the identification information indicated by the vehicle number plate 27. In this case, the analyzing unit 14 of the server 4 extracts the information corresponding to the identification information indicated by the vehicle number plate 27 from the storage unit 13. Thus, in addition to the advantages of the first to third exemplary embodiments, it is possible to identify a secondary battery to be compared even when the identification information (the battery system ID) is not transmitted from the connected battery system.

Fifth Exemplary Embodiment

In the first to third exemplary embodiments, a case where the battery system is identified using the battery system ID notified from the battery system 2 has been described. The fifth exemplary embodiment is different from the first to third exemplary embodiments in that the number unique to an on-vehicle device attached on the electric-powered vehicle 1 on which the battery system 2 is mounted is used as the identification information (ID) of the battery system.

Figure 10:
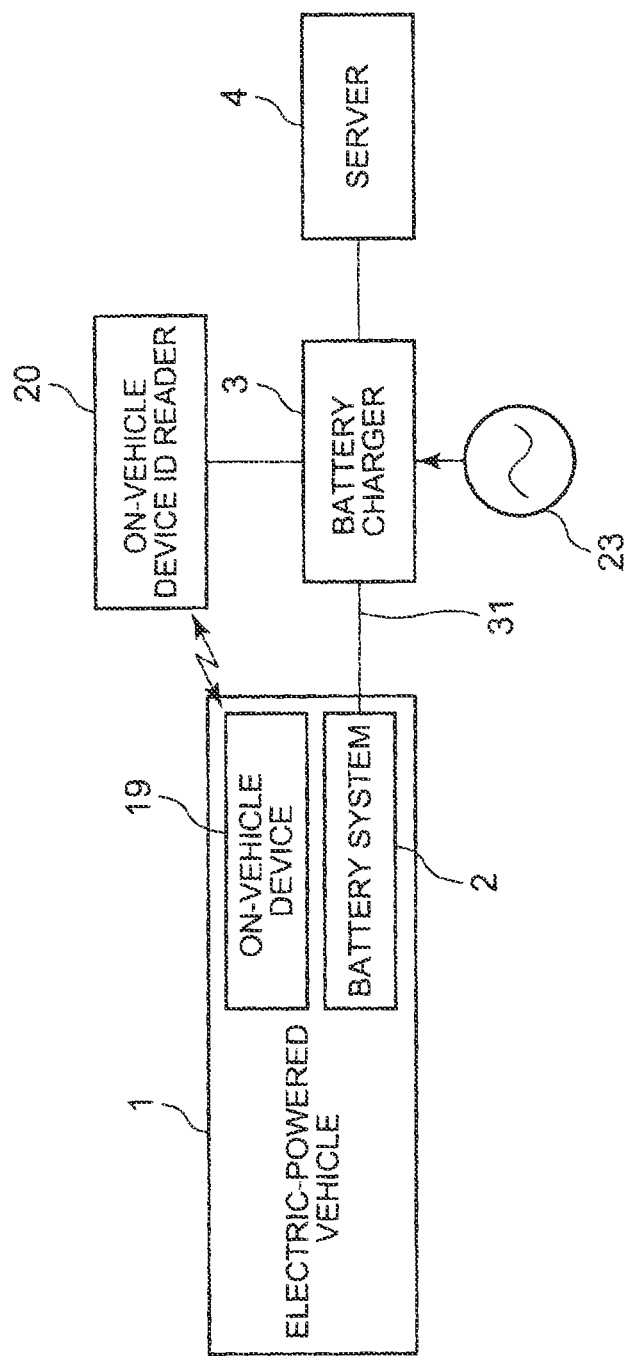
[FIG. 10] It depicts a block diagram illustrating an example of a secondary battery state management system according to a fifth embodiment of the present invention.

FIG. 10 is a block diagram illustrating an example of a secondary battery state management system according to the fifth exemplary embodiment. The secondary battery state management system of the present exemplary embodiment includes the battery system 2, the battery charger 3, the server 4, an on-vehicle device 19, and an on-vehicle device ID reader 20. The battery system 2 and the on-vehicle device 19 are mounted on the electric-powered vehicle 1. Moreover, the battery charger 3 and the on-vehicle device ID reader 20 are connected to each other. The other configurations are the same as those of the first to third exemplary embodiments.

The on-vehicle device 19 is a device with a wireless interface, to which a unique number is assigned. The on-vehicle device 19 transmits the unique number assigned to each on-vehicle device to the on-vehicle device ID reader 20 via a wireless interface. The unique number of the on-vehicle device may be a unique number that is assigned to the on-vehicle device itself, and may be a unique number assigned to a card that is inserted in the on-vehicle device, for example.

The on-vehicle device 19 is realized by an on-vehicle device or the like that is used in an Electronic Toll Collection System (ETC), for example.

Moreover, Dedicated Short Range Communication (DSRC), for example, is used as the wireless interface that is used when transmitting the unique number. However, the wireless interface is not limited to the DSRC.

The on-vehicle device ID reader 20 is a device that reads the unique number of the on-vehicle device 19, transmitted via the wireless interface. The on-vehicle device ID reader 20 is used in the ETC, for example, and is realized by a road-side DSRC device that is disposed in a base station. However, the exemplary embodiment of the on-vehicle device ID reader 20 is not limited to the road-side DSRC device.

As above, the fifth exemplary embodiment is different from the first exemplary embodiment in that the on-vehicle device 19 with the wireless interface, to which a unique number is assigned, is mounted on the electric-powered vehicle 1, the on-vehicle device ID reader 20 that reads the unique number of the on-vehicle device 19 via the wireless interface (and a radio communication line) is connected to the battery charger 3, and the unique number of the on-vehicle device 19 is used instead of the battery system ID.

Next, the operation of the fifth exemplary embodiment will be described. In the following description, a case where rather than acquiring the battery system ID from the battery system 2 as in the first exemplary embodiment, the unique number of the on-vehicle device 19 is acquired will be described.

Figure 11:
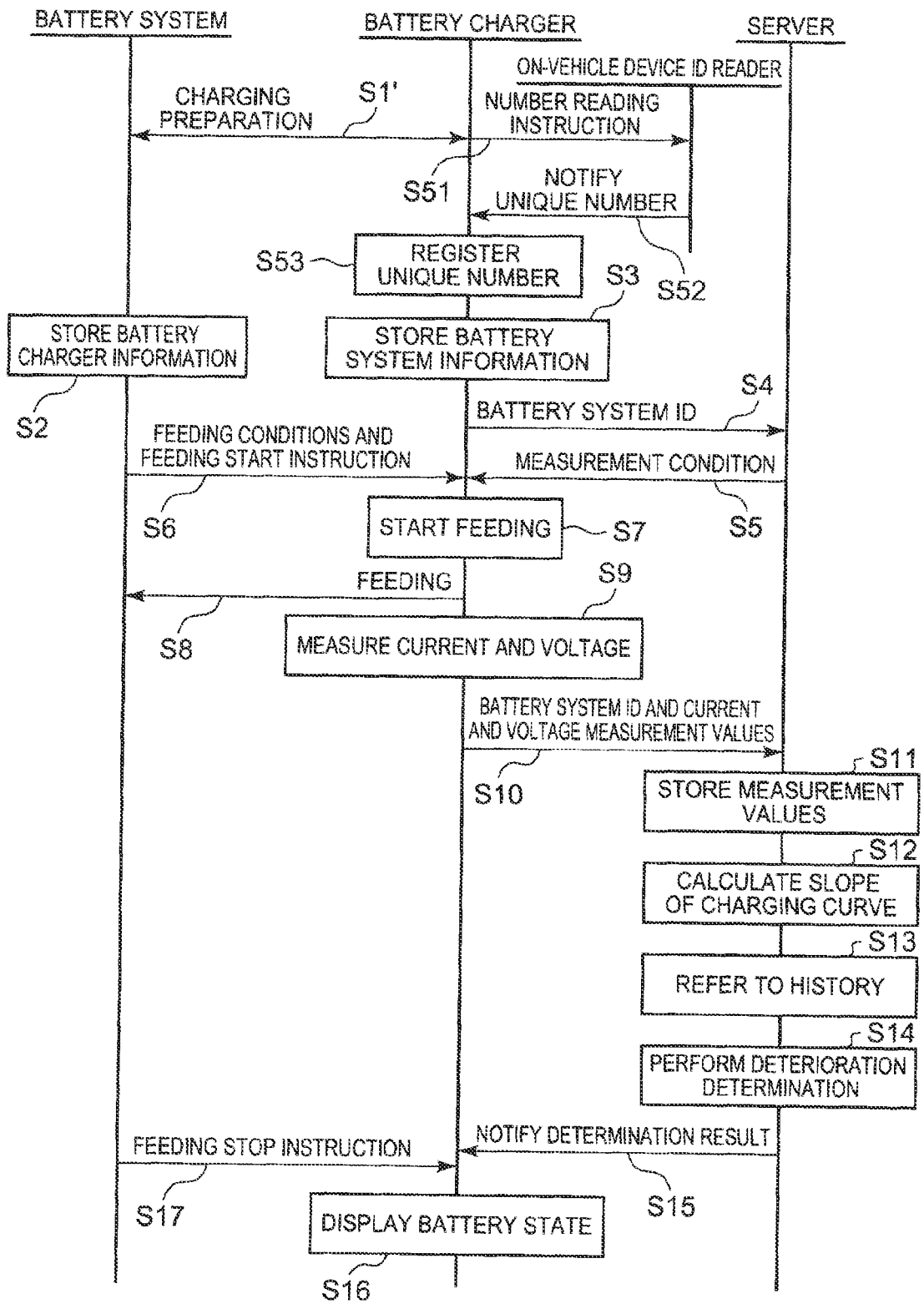
[FIG. 11] It depicts a sequence diagram illustrating an example of an operation of acquiring the unique number of an on-vehicle device 19.

FIG. 11 is a sequence diagram illustrating an example of the operation of acquiring the unique number of the on-vehicle device 19 instead of the battery system ID.

When the battery charger 3 is connected to the battery system 2, a charging preparation process is executed between the battery system 2 and the battery charger 3 in a manner similarly to the first to third exemplary embodiments (step S1'). This process is different from the process of step S1 of FIG. 3 in that the battery system ID is not notified to the battery charger 3.

Moreover, in parallel with the charging preparation process, the control unit 10 of the battery charger 3 instructs the on-vehicle device ID reader 20 to read the unique number of the on-vehicle device 19 (step S51). The on-vehicle device ID reader 20 communicates with the on-vehicle device 19 via the wireless interface and acquires the unique number of the on-vehicle device 19 (step S52). Upon acquiring the unique number, the control unit 10 of the battery charger 3 stores the value in the memory unit 25 (step S53).

As described above, the on-vehicle device 19 and the on-vehicle device ID reader 20 of the present exemplary embodiment are the on-vehicle device and the base station of the Electronic Toll Collection System (ETC), for example, and an example of the wireless interface includes the DSRC.

The processes of performing deterioration determination based on the measured values are the same as the processes of steps S2 to S17 illustrated in FIG. 3. However, it should be noted that in the respective processes, the unique number of the on-vehicle device 19 is used instead of the battery system ID.

In the above description, a case where the process of acquiring the unique number from the on-vehicle device 19 and the process of using the unique number instead of the battery system ID are performed in parallel with the charging preparation process of the first exemplary embodiment has been described. These processes can be applied to the second and third exemplary embodiments as well as the first exemplary embodiment.

As described above, according to the present exemplary embodiment, when the battery charger 3 is connected to the secondary battery 5, the battery charger 3 receives the on-vehicle device ID of the on-vehicle device 19 provided to the electric-powered vehicle 1, on which the secondary battery 5 is mounted, from the on-vehicle device ID reader 20 that receives the on-vehicle device ID from the battery charger 3 via a radio communication circuit. Moreover, the measuring unit 9 of the battery charger 3 identifies the secondary battery of which the electrical characteristics are to be measured based on the on-vehicle device ID of the on-vehicle device 19. In this case, the analyzing unit 14 of the server 4 extracts the information corresponding to the on-vehicle device ID from the storage unit 13. Thus, similarly to the fourth exemplary embodiment, in addition to the advantages of the first to third exemplary embodiments, it is possible to identify a secondary battery to be compared even when the identification information (the battery system ID) is not transmitted from the connected battery system.

Sixth Exemplary Embodiment

In the first to third exemplary embodiments, a case where the battery system is identified using the battery system ID notified from the battery system 2 has been described. In a sixth exemplary embodiment, it is different from the first to third exemplary embodiments in that a card ID assigned to a card associated with the battery system is used as the identification information (ID) of the battery system.

Here, the card associated with the battery system is a card that is determined for each battery system, and the battery system can be identified by the unique identification information assigned to the card. Hereinafter, the unique identification information assigned to the card will be referred to as a card ID.

Figure 12:
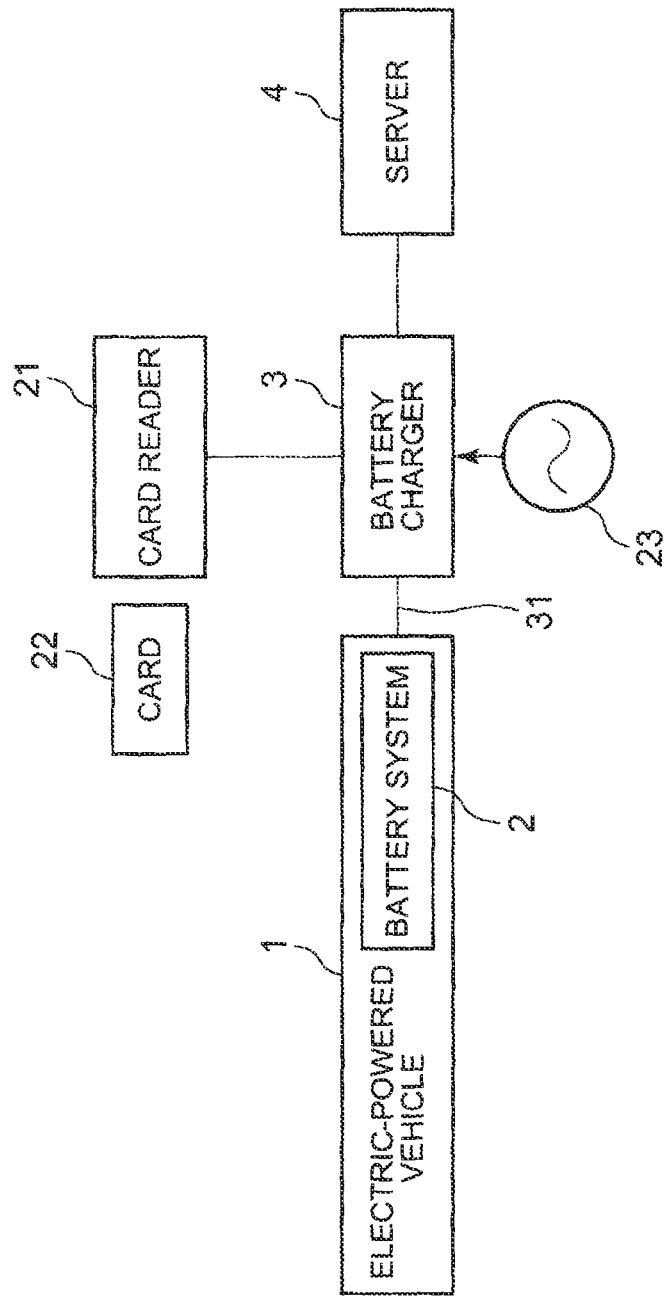
[FIG. 12] It depicts a block diagram illustrating an example of a secondary battery state management system according to a sixth embodiment of the present invention.

FIG. 12 is a block diagram illustrating an example of a secondary battery state management system according to the sixth exemplary embodiment. The secondary battery state management system of the present exemplary embodiment includes the battery system 2, the battery charger 3, the server 4, and a card reader 21. The battery charger 3 and the card reader 21 are connected to each other. Further, a card 22 is associated in advance with the battery system 2, and is carried by a driver of the electric-powered vehicle 1, for example. The other configurations are the same as those of the first to third exemplary embodiments.

The card 22 is a card that is associated with the battery system 2. The card 22 is realized by an IC card that stores the card ID, for example. The card reader 21 recognizes the card ID assigned to the card 22 and notifies the recognized card ID to the battery charger 3. Specifically, when the card in which the card ID is stored is swiped through the card reader 21, the card reader 21 reads the card ID stored in the card. Moreover, the card reader 21 notifies the read card ID to the battery charger.

When an IC card is used as the card 22, the card reader 21 may be realized by an IC card reader. However, the exemplary embodiment of the card reader 21 is not limited to the IC card reader.

As above, the sixth exemplary embodiment is different from the first exemplary embodiment in that the card reader 21 that acquires the card ID of the card 22 is connected to the battery charger 3, and the card ID of the card 22 is used instead of the battery system ID.

Next, the operation of the sixth exemplary embodiment will be described. In the following description, a case where rather than acquiring the battery system ID from the battery system 2 as in the first exemplary embodiment, the card ID assigned to the card 22 is acquired will be described.

Figure 13:
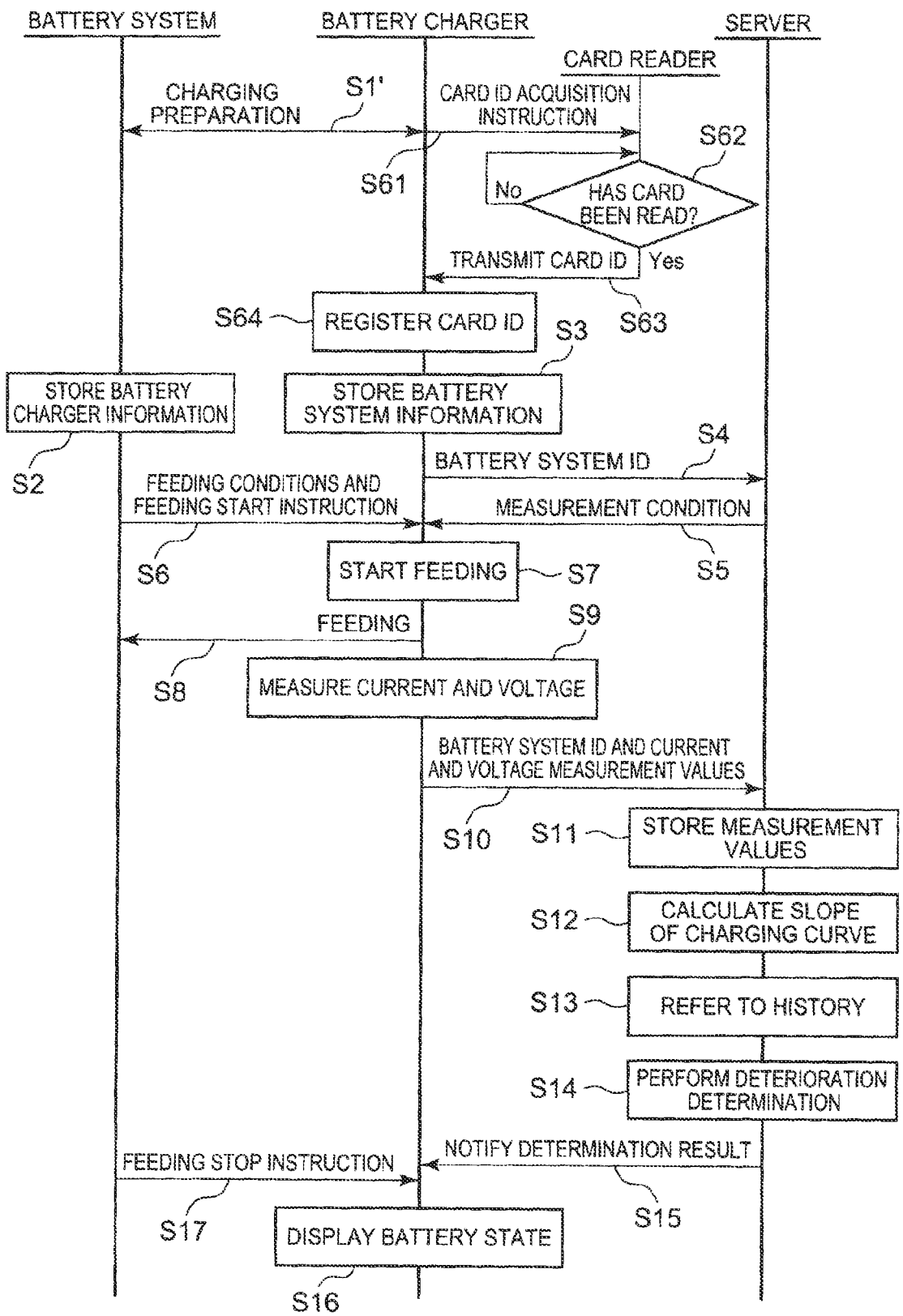
[FIG. 13] It depicts a sequence diagram illustrating an example of an operation of acquiring a card ID.

FIG. 13 is a sequence diagram illustrating an example of the operation of acquiring the card ID instead of the battery system ID.

When the battery charger 3 is connected to the battery system 2, a charging preparation process is executed between the battery system 2 and the battery charger 3 in a manner similarly to the first to third exemplary embodiments (step S1'). This process is different from the process of step S1 of FIG. 3 in that the battery system ID is not notified to the battery charger 3.

Moreover, in parallel with the charging preparation process, the control unit 10 of the battery charger 3 instructs the card reader 21 to acquire the card ID assigned to the card 22 (step S61). The card reader 21 is in a standby state until the card reader 21 reads the information of the card 22. That is, the card reader 21 determines whether the information of the card 22 is read or not (step S62), and when the information is not read (No in step S62), the card reader 21 repeats the process of step S62.

After that, when the card 22 is swiped through the card reader (Yes in step S62), the card reader 21 notifies the read card ID to the battery charger 3 (step S63). Here, it can be said that the information of the card 22 is read by the card reader 21 when the card 22 is swiped through the card reader. The control unit 10 of the battery charger 3 stores the received card ID in the memory unit 25 (step S64).

The processes of performing deterioration determination based on the measured values are the same as the processes of steps S2 to S17 illustrated in FIG. 3. It should be noted that in the respective processes, the card ID of the card 22 is used instead of the battery system ID.

In the above description, a case where the process of acquiring the card ID from the card 22 and the process of using the card ID instead of the battery system ID are performed in parallel with the charging preparation process of the first exemplary embodiment has been described. These processes can be applied to the second and third exemplary embodiments as well as the first exemplary embodiment.

As described above, according to the exemplary embodiment, the battery charger 3 receives the card ID assigned to the card 22 that is associated with the secondary battery 5, from the card reader 21. Moreover, the measuring unit 9 of the battery charger 3 identifies the secondary battery of which the electrical characteristics are to be measured based on the received card ID. In this case, the analyzing unit 14 of the server 4 extracts the information corresponding to the card ID from the storage unit 13. Thus, similarly to the fourth and fifth exemplary embodiments, in addition to the advantages of the first to third exemplary embodiments, it is possible to identify a secondary battery to be compared even when the identification information (the battery system ID) is not transmitted from the connected battery system.

Figure 14:
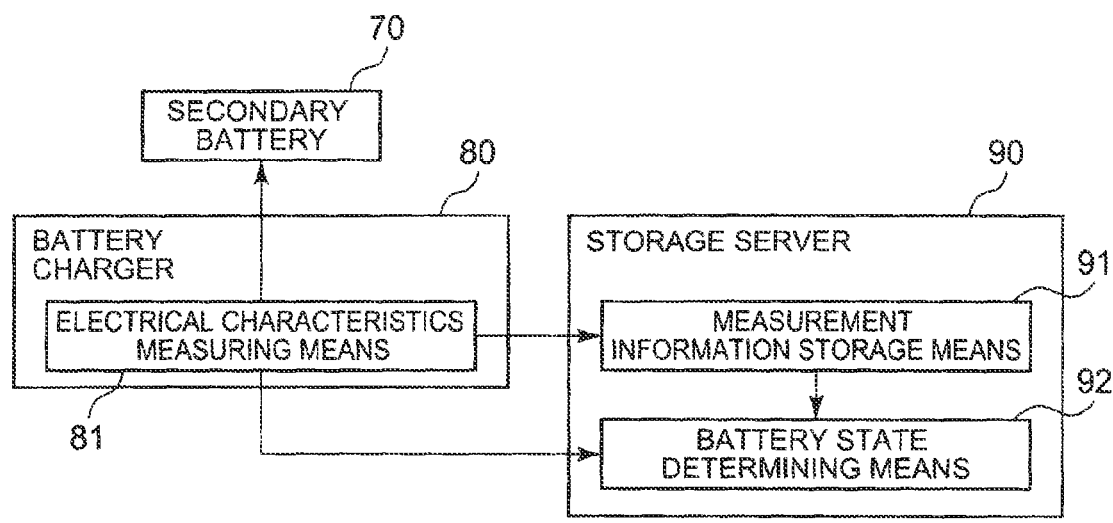
[FIG. 14] It depicts a block diagram illustrating an example of a minimal configuration of the secondary battery state management system according to the present invention.

Next, an example of minimal configuration of the secondary battery state management system according to the invention will be described. FIG. 14 is a block diagram illustrating an example of minimal configuration of the secondary battery state management system according to the invention. The secondary battery state management system according to the invention includes a battery charger 80 (for example, the battery charger 3) that charges a secondary battery 70 (for example, the secondary battery 5) and a storage server 90 (for example, the server 4) that stores electrical characteristic information (for example, a current value, a voltage value, an electric energy, an impedance, or the like) which is the information that indicates the electrical characteristics during charging of the secondary battery 70.

The battery charger 80 includes electrical characteristic measuring means 81 (for example, the measuring unit 9) that measures the electrical characteristics during charging.

The storage server 90 includes measurement information storage means 91 (for example, the storage unit 13) that stores the history of the measured electrical characteristic information for each secondary battery and battery state determining means 92 (for example, the analyzing unit 14) that compares the electrical characteristic information of the secondary battery being measured by the electrical characteristic measuring means 81 with the electrical characteristic information of the same secondary battery stored in the measurement information storage means 91 and determines the state of the secondary battery.

With such a configuration, it is possible to manage the state of the secondary battery during charging. Specifically, even when information such as charging characteristics is not acquired from the battery system, it is possible to collect information necessary for estimating the deterioration state of the secondary battery. Moreover, by analyzing the collected information, it is possible to estimate the deterioration state and prompt the user to take inspection. Thus, safety is improved.

Moreover, the electrical characteristic measuring means 81 of the battery charger 80 may measure a value of a voltage value between power feeding lines (for example, the power feeding lines 31) that connect the secondary battery and the battery charger and at least one of a value of the current value that flows through the power feeding lines, and the electric energy as the electrical characteristics.

Moreover, the battery charger 80 may include AC signal superimposing means (for example, the AC impedance measurement signal source 26) that superimposes an AC signal on the power feeding lines that connect the secondary battery and the battery charger. Moreover, when the AC signal is superimposed on the power feeding lines, the electrical characteristic measuring means 81 of the battery charger 80 may calculate an impedance (for example, an AC impedance) based on an AC voltage between the power feeding lines and the AC signal, the measurement information storage means 91 of the storage server 90 may store the history of the calculated impedance for each secondary battery, and the battery state determining means 92 of the storage server 90 may compare the calculated impedance with the impedance of the same secondary battery, stored in the measurement information storage means 91 to determine the state of the secondary battery (for example, determine that the secondary battery deteriorates when the impedance increases).

Moreover, the battery state determining means 92 of the storage server 90 may determine the state of the secondary battery 70 by comparing the electrical characteristic information of the secondary battery 70 being measured by the electrical characteristic measuring means 81 with the electrical characteristic information of the secondary battery 70 of which the voltage value and the current value stored in the measurement information storage means 91 are the same in terms of a change of the voltage value per single time.

Moreover, the battery state determining means 92 of the storage server 90 may determine the state of the secondary battery by comparing the electrical characteristic information of the secondary battery 70 being measured by the electrical characteristic measuring means 81 with the electrical characteristic information of the secondary battery 70, stored in the measurement information storage means 91 in terms of the electric energy supplied to the secondary battery 70 with a change of a predetermined voltage value (for example, measurement conditions).

Moreover, the storage server 90 may include registration processing means (for example, the analyzing unit 14) that receives the electrical characteristic information of the secondary battery measured by the electrical characteristic measuring means 81 of the battery charger 80 and at least one item of information among items of information that are calculated based on the electrical characteristic information from the battery charger along with identification information (for example, the battery system ID) of the secondary battery and stores the received information in the measurement information storage means 91.

Moreover, the electrical characteristic measuring means 81 of the battery charger 80 may identify a secondary battery of which the electrical characteristics are to be measured based on the identification information (for example, the battery system ID) of the secondary battery 70 notified when the battery charger 80 is connected to the secondary battery 70, the measurement information storage means 91 of the storage server 90 may store the history of the measured electrical characteristic information of the secondary battery for each item of the identification information of the secondary battery, and the battery state determining means 92 of the storage server 90 may extract the electrical characteristic information corresponding to the identification information of the secondary battery from the measurement information storage means 91.

Moreover, the electrical characteristic measuring means 81 of the battery charger 80 may receive an identification number of a moving vehicle read by a moving vehicle identification number reading means (for example, the vehicle number reader 17) that reads the identification number (for example, the vehicle number plate 27) that is expressed on the moving vehicle (for example, the electric-powered vehicle 1), on which the secondary battery 70 is mounted, when the battery charger 80 is connected to the secondary battery 70, and may identify the secondary battery of which the electrical characteristics are to be measured based on the identification number of the moving vehicle, the measurement information storage means 91 of the storage server 90 may store the history of the measured electrical characteristic information of the secondary battery for each identification number of the moving vehicle, and the battery state determining means 92 of the storage server 90 may extract the electrical characteristic information corresponding to the identification number of the moving vehicle from the measurement information storage means 91.

Moreover, the electrical characteristic measuring means 81 of the battery charger 80 may receive identification information (for example, an on-vehicle device ID) of an on-vehicle device (for example, the on-vehicle device 19) provided to a moving vehicle (for example, the electric-powered vehicle 1), on which the secondary battery 70 is mounted, from an on-vehicle device identification information detection means (for example, the on-vehicle device ID reader 20) that receives the identification information from the battery charger 80 via a radio communication line when the battery charger 80 is connected to the secondary battery 70 and may identify a secondary battery of which the electrical characteristics are to be measured based on the received identification information of the on-vehicle device, the measurement information storage means 91 of the storage server 90 may store the history of the measured electrical characteristic information of the secondary battery for each identification information of the on-vehicle device, and the battery state determining means 92 of the storage server 90 may extract the electrical characteristic information corresponding to the identification information of the on-vehicle device from the measurement information storage means.

Moreover, the electrical characteristic measuring means 81 of the battery charger 80 may receive unique identification information (for example, a card ID) assigned to a medium (for example, the card 22) associated to the secondary battery 70 from a medium identification information reading means (for example, the card reader 21) that reads the identification information of the medium and may identify a secondary battery of which the electrical characteristics are to be measured based on the received identification information of the medium, the measurement information storage means 91 of the storage server 90 may store the history of the measured electrical characteristic information of the secondary battery for each identification information of the medium, and the battery state determining means 92 of the storage server 90 may extract the electrical characteristic information corresponding to the identification information of the medium from the measurement information storage means.

Moreover, the battery state determining means 92 may use at least one of a surface temperature of the secondary battery 70 and an ambient temperature of the battery charger 80 in determining the state of the secondary battery 70.

Figure 15:
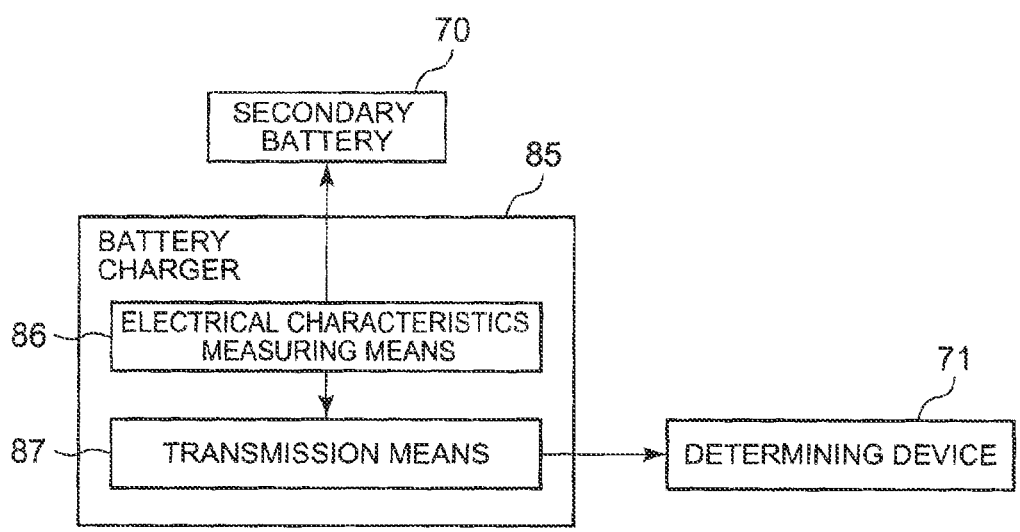
[FIG. 15] It depicts a block diagram illustrating an example of a minimal configuration of the battery charger according to the present invention.

Next, an example of a minimal configuration of the battery charger according to the invention will be described. FIG. 15 is a block diagram illustrating an example of a minimal configuration of the battery charger according to the invention. A battery charger 85 according to the invention is a battery charger that charges the secondary battery 70 connected thereto, and includes electrical characteristic measuring means 86 (for example, the measuring unit 9) that measures the electrical characteristics during charging of the secondary battery 70 and transmission means 87 that transmits electrical characteristic information (for example, a current value, a voltage value, an electric energy, an impedance, or the like) which is the information that indicates the electrical characteristics of the secondary battery, measured by the electrical characteristic measuring means 86 to a determining device 71 (for example, the server 4) that determines the state of the secondary battery by comparing the received electrical characteristic information with the stored history of the electrical characteristic information of the same secondary battery.

With such a configuration, it is also possible to manage the state of the secondary battery during charging.

Moreover, the electrical characteristic measuring means 86 may measure a value of a voltage between power feeding lines (for example, the power feeding lines 31) that connect the secondary battery 70 and the battery charger 85 and at least one of a value of a current that flows through the power feeding lines and the electric energy as the electrical characteristics.

Part or all of the above exemplary embodiments can be expressed as the following notes, but the invention is not limited thereto.

(Supplementary note 1) A secondary battery state management system including: a battery charger that charges a secondary battery; and a storage server that stores electrical characteristic information which is information that indicates electrical characteristics during charging of the secondary battery, in which the battery charger includes an electrical characteristic measuring means that measures the electrical characteristics during charging, and in which the storage server includes a measurement information storage means that stores the history of the measured electrical characteristic information for each secondary battery, and a battery state determining means that compares the electrical characteristic information of the secondary battery being measured by the electrical characteristic measuring means with electrical characteristic information of the same secondary battery stored in the measurement information storage means and determines the state of the secondary battery.

(Supplementary note 2) The secondary battery state management system according to Supplementary note 1, in which the electrical characteristic measuring means of the battery charger measures a value of a voltage value between power feeding lines that connect the secondary battery and the battery charger and at least one of a value of a current value that flows through the power feeding lines and an electric energy as the electrical characteristics.

(Supplementary note 3) The secondary battery state management system according to Supplementary note 1 or 2, in which the battery charger includes an AC signal superimposing means that superimposes an AC signal on the power feeding lines that connect the secondary battery and the battery charger, in which the electrical characteristic measuring means of the battery charger calculates an impedance based on the AC signal and an AC voltage between the power feeding lines when the AC signal is superimposed on the power feeding lines, in which the measurement information storage means of the storage server stores the history of the calculated impedance for each secondary battery, and in which the battery state determining means of the storage server compares the calculated impedance with the impedance of the same secondary battery, stored in the measurement information storage means to determine the state of the secondary battery.

(Supplementary note 4) The secondary battery state management system according to Supplementary note 1 or 2, in which the battery state determining means of the storage server determines the state of the secondary battery by comparing the electrical characteristic information of the secondary battery being measured by the electrical characteristic measuring means with the electrical characteristic information of the secondary battery of which the voltage value and the current value stored in the measurement information storage means are the same in terms of a change of the voltage value per single time.

(Supplementary note 5) The secondary battery state management system according to Supplementary note 1 or 2, in which the battery state determining means of the storage server determines the state of the secondary battery by comparing the electrical characteristic information of the secondary battery being measured by the electrical characteristic measuring means with the electrical characteristic information of the secondary battery stored in the measurement information storage means in terms of the electric energy supplied to the secondary battery with a change of a predetermined voltage value.

(Supplementary note 6) The secondary battery state management system according to any one of Supplementary notes 1 to 5, in which the storage server includes a registration processing means that receives the electrical characteristic information of the secondary battery measured by the electrical characteristic measuring means of the battery charger and at least one item of information among items of information that are calculated based on the electrical characteristic information from the battery charger along with identification information of the secondary battery and stores the received information in the measurement information storage means.

(Supplementary note 7) The secondary battery state management system according to any one of Supplementary notes 1 to 6, in which the electrical characteristic measuring means of the battery charger identifies a secondary battery of which electrical characteristics are to be measured based on the identification information of the secondary battery notified when the battery charger is connected to the secondary battery, in which the measurement information storage means of the storage server stores the history of the measured electrical characteristic information of the secondary battery for each identification information of the secondary battery, and in which the battery state determining means of the storage server extracts the electrical characteristic information corresponding to the identification information of the secondary battery from the measurement information storage means.

(Supplementary note 8) The secondary battery state management system according to any one of Supplementary notes 1 to 6, in which the electrical characteristic measuring means of the battery charger receives an identification number of a moving vehicle read by a moving vehicle identification number reading means that reads the identification number expressed on the moving vehicle on which the secondary battery is mounted when the battery charger is connected to the secondary battery and identifies a secondary battery of which the electrical characteristics are to be measured based on the identification number of the moving vehicle, in which the measurement information storage means of the storage server stores the history of the measured electrical characteristic information of the secondary battery for each identification number of the moving vehicle, and in which the battery state determining means of the storage server extracts the electrical characteristic information corresponding to the identification number of the moving vehicle from the measurement information storage means.

(Supplementary note 9) The secondary battery state management system according to any one of Supplementary notes 1 to 6, in which the electrical characteristic measuring means of the battery charger receives identification information of an on-vehicle device provided to a moving vehicle, on which the secondary battery is mounted, from an on-vehicle device identification information detection means that receives the identification information from the battery charger via a radio communication line when the battery charger is connected to the secondary battery and identifies a secondary battery of which the electrical characteristics are to be measured based on the received identification information of the on-vehicle device, in which the measurement information storage means of the storage server stores the history of the measured electrical characteristic information of the secondary battery for each identification information of the on-vehicle device, and in which the battery state determining means of the storage server extracts the electrical characteristic information corresponding to the identification information of the on-vehicle device from the measurement information storage means.

(Supplementary note 10) The secondary battery state management system according to any one of Supplementary notes 1 to 6, in which the electrical characteristic measuring means of the battery charger receives unique identification information assigned to a medium associated with a secondary battery from a medium identification information reading means that reads the identification information of the medium, and identifies a secondary battery of which the electrical characteristics are to be measured based on the received identification information of the medium, in which the measurement information storage means of the storage server stores the history of the measured electrical characteristic information of the secondary battery for each identification information of the medium, and in which the battery state determining means of the storage server extracts the electrical characteristic information corresponding to the identification information of the medium from the measurement information storage means.

(Supplementary note 11) The secondary battery state management system according to any one of Supplementary notes 1 to 10, in which the battery state determining means uses at least one of a surface temperature of the secondary battery and an ambient temperature of the battery charger in determining the state of the secondary battery.

(Supplementary note 12) A battery charger that charges a secondary battery, including: an electrical characteristic measuring means that measures electrical characteristics during charging of the secondary battery; and a transmission means that transmits electrical characteristic information which is information that indicates the electrical characteristics of the secondary battery measured by the electrical characteristic measuring means to a determining device that compares the received electrical characteristic information with the stored history of the electrical characteristic information of the same secondary battery to determine the state of the secondary battery.

(Supplementary note 13) The battery charger according to Supplementary note 12, in which the electrical characteristic measuring means measures a voltage value between power feeding lines that connect the secondary battery and the battery charger and at least one of a current value that flows through the power feeding lines, power and an electric energy as the electrical characteristics.

(Supplementary note 14) A secondary battery state management method including: allowing a battery charger that charges a secondary battery to measure electrical characteristics during charging; and allowing a storage server that includes a measurement information storage means that stores the history of electrical characteristic information which is information indicating the electrical characteristics for each secondary battery to compare the electrical characteristic information of the secondary battery measured during charging with the electrical characteristic information of the same secondary battery stored in the measurement information storage means to determine the state of the secondary battery.

(Supplementary note 15) The secondary battery state management method according to Supplementary note 14, in which when measuring the electrical characteristics, a voltage value between power feeding lines that connect the secondary battery and the battery charger and at least one of a current value that flows through the power feeding lines, power and an electric energy are measured as the electrical characteristics.

(Supplementary note 16) An electrical characteristics measurement method including: allowing a battery charger that charges a secondary battery to measure electrical characteristics during charging of the secondary battery; and allowing the battery charger to transmit electrical characteristic information which is information that indicates the measured electrical characteristics of the secondary battery to a determining device that compares the received electrical characteristic information with the stored history of the electrical characteristic information of the same secondary battery to determine the state of the secondary battery.

(Supplementary note 17) The electrical characteristics measurement method according to Supplementary note 16, in which when measuring the electrical characteristics, a voltage value between power feeding lines that connect the secondary battery and the battery charger and at least one of a current value that flows through the power feeding lines, power and an electric energy are measured as the electrical characteristics.

(Supplementary note 18) An electrical characteristics measurement program that is mounted on a computer that charges a secondary battery, the electrical characteristics measurement program causing the computer to execute: an electrical characteristics measurement process for measuring electrical characteristics during charging of the secondary battery; and a transmission process for transmitting electrical characteristic information which is information that indicates the electrical characteristics of the secondary battery measured in the electrical characteristics measurement process to a determining device that compares the received electrical characteristic information with the stored history of the electrical characteristic information of the same secondary battery to determine the state of the secondary battery.

(Supplementary note 19) The electrical characteristics measurement program according to Supplementary note 18, in which in the electrical characteristics measurement process, a voltage between power feeding lines that connect the secondary battery and the battery charger and at least one of a current that flows through the power feeding lines, power and an electric energy are measured as the electrical characteristics.

Although the present invention has been described with reference to the exemplary embodiments and examples, the present invention is not limited to the exemplary embodiments and examples described above. Various modifications which can be understood by one skilled in the art can be made in the configuration and details of the present invention within the scope of the present invention.

This application is based upon and claims the benefit of priority from Japanese patent application No. 2010-101223, filed on Apr. 26, 2010, the disclosure of which is incorporated herein in its entirety by reference.

Industrial Applicability

The invention is suitably applied to a secondary battery state management system that manages the state of a secondary battery that is mounted on an electric-powered vehicle or the like.

REFERENCE SIGNS LIST

1: Electric-powered vehicle
2: Battery system
3: Battery charger
4: Server
5: Secondary battery
6: Control unit (Battery system 2)
7: Communication unit (Battery system 2)
8: Power supply unit
9: Measuring unit
10: Control unit (Battery charger 3)
11: Communication unit (Battery charger 3)
12: Display unit
13: Storage unit
14: Analyzing unit
15: Communication unit (Server 4)
17: Vehicle number reader
18: Camera
19: On-vehicle device
20: On-vehicle device ID reader
21: Card reader
22: Card
23: Commercial power supply
24: Memory Unit (Battery system 2)
25: Memory Unit (Battery charger 3)
26: AC impedance measurement signal source
27: Vehicle number plate
31: Power feeding line

The invention claimed is:

1. A secondary battery state management system comprising:
   a battery charger that charges a secondary battery,
   wherein the battery charger comprises:
      an electrical characteristic measuring unit comprising a memory and a processor which executes operations based on code stored in the memory, the operations comprising determining a measurement condition for the second battery and measuring an electrical characteristic during charging based on the determined measurement condition; and
   a storage server comprising:
      a measurement information storage unit that stores a history of the electrical characteristic for the secondary battery, and
      a battery state determining unit, implemented by the processor, that determines a state of the secondary battery based on the measured electrical characteristic and the history of the electrical characteristic that is stored in the measurement information storage unit and corresponds to the secondary battery.

2. The secondary battery state management system according to claim 1,
   wherein the electrical characteristic measuring unit of the battery charger measures a voltage value between power feeding lines that connect the secondary battery and the battery charger and at least one of a current value that flows through the power feeding lines, power and an electric energy as the electrical characteristics.

3. The secondary battery state management system according to claim 1,
   wherein the battery charger includes an AC signal superimposing unit that superimposes an AC signal on the power feeding lines that connect the secondary battery and the battery charger,
   the electrical characteristic measuring unit of the battery charger calculates an impedance based on the AC signal and an AC voltage between the power feeding lines when the AC signal is superimposed on the power feeding lines,
   the measurement information storage unit of the storage server stores the history of the calculated impedance for the secondary battery, and
   the battery state determining unit of the storage server compares the calculated impedance with the impedance of the same secondary battery, stored in the measurement information storage unit to determine the state of the secondary battery.

4. The secondary battery state management system according to claim 1,
   wherein the battery state determining unit of the storage server determines the state of the secondary battery by comparing the measured electrical characteristic with the electrical characteristic of the secondary battery of which the voltage value and the current value stored in the measurement information storage unit are the same in terms of a change of the voltage value per single time.

5. The secondary battery state management system according to claim 1,
   wherein the battery state determining unit of the storage server determines the state of the secondary battery by comparing the measured electrical characteristic with the electrical characteristic of the secondary battery stored in the measurement information storage unit in terms of the electric energy supplied to the secondary battery with a change of a predetermined voltage value.

6. The secondary battery state management system according to claim 1,
   wherein the storage server includes a registration processing unit that receives the measured electrical characteristic and at least one item of information among items of information that are calculated based on the electrical characteristic from the battery charger along with identification information of the secondary battery and stores the received information in the measurement information storage unit.

7. The secondary battery state management system according to claim 1,
   wherein the electrical characteristic measuring unit of the battery charger identifies a secondary battery of which electrical characteristics are to be measured based on the identification information of the secondary battery notified when the battery charger is connected to the secondary battery,
   the measurement information storage unit of the storage server stores the history of the measured electrical characteristic of the secondary battery for the identification information of the secondary battery, and
   the battery state determining unit of the storage server extracts the electrical characteristic corresponding to the identification information of the secondary battery from the measurement information storage unit.

8. The secondary battery state management system according to claim 1,
   wherein the electrical characteristic measuring unit of the battery charger receives an identification number of a moving vehicle read by a moving vehicle identification number reading unit that reads the identification number expressed on the moving vehicle on which the secondary battery is mounted when the battery charger is connected to the secondary battery and identifies a secondary battery of which the electrical characteristics are to be measured based on the identification number of the moving vehicle,
   the measurement information storage unit of the storage server stores the history of the measured electrical characteristic of the secondary battery for the identification number of the moving vehicle, and
   the battery state determining unit of the storage server extracts the electrical characteristic corresponding to the identification number of the moving vehicle from the measurement information storage unit.

9. The secondary battery state management system according to claim 1,
   wherein the electrical characteristic measuring unit of the battery charger receives identification information of an on-vehicle device provided to a moving vehicle, on which the secondary battery is mounted, from an on-vehicle device identification information detection unit that receives the identification information from the battery charger via a radio communication line when the battery charger is connected to the secondary battery and identifies a secondary battery of which the electrical characteristics are to be measured based on the received identification information of the on-vehicle device,
   the measurement information storage unit of the storage server stores the history of the measured electrical characteristic of the secondary battery for the identification information of the on-vehicle device, and
   the battery state determining unit of the storage server extracts the electrical characteristic corresponding to the identification information of the on-vehicle device from the measurement information storage unit.

10. The secondary battery state management system according to claim 1,
wherein the electrical characteristic measuring unit of the battery charger receives unique identification information assigned to a medium associated with a secondary battery from medium identification information reading unit that reads the identification information of the medium, and identifies a secondary battery of which the electrical characteristics are to be measured based on the received identification information of the medium,
the measurement information storage unit of the storage server stores the history of the measured electrical characteristic of the secondary battery for the identification information of the medium, and
the battery state determining unit of the storage server extracts the electrical characteristic corresponding to the identification information of the medium from the measurement information storage unit.

11. The secondary battery state management system according to claim 1,
wherein the battery state determining unit uses at least one of a surface temperature of the secondary battery and an ambient temperature of the battery charger in determining the state of the secondary battery.

12. The secondary battery state management system according to claim 1,
wherein the battery charger acquires the measurement condition determined for the secondary battery from the storage server.

13. The secondary battery state management system according to claim 1,
wherein the electrical characteristic measuring unit measures a value of the voltage or a value of the current as the electrical characteristics in a discrete manner based on the measurement condition.

14. The secondary battery state management system according to claim 1,
wherein the measurement condition is determined for the identification information of the secondary battery, for a type of vehicle which mounts the secondary battery, or for manufacturer information.

15. A battery charger comprising:
an electrical characteristic measuring unit comprising a memory and a processor which executes operations based on code stored in the memory, the operations comprising determining a measurement condition for a secondary battery and measuring an electrical characteristic during charging of the secondary battery based on the determined measurement condition; and
a transmission unit, implemented by the processor, that transmits an electrical characteristic of the secondary battery measured by the electrical characteristic measuring unit to a determining device that determines a state of the secondary battery based on the measured electrical characteristic and a stored history of the electrical characteristic corresponding to the secondary battery.

16. The battery charger according to claim 15,
wherein the electrical characteristic measuring unit measures a voltage value between power feeding lines that connect the secondary battery and the battery charger and at least one of a current value that flows through the power feeding lines, power and an electric energy as the electrical characteristics.

17. The battery charger according to claim 15,
wherein the electrical characteristic measuring unit acquires the measurement condition determined for the secondary battery.

18. The battery charger according to claim 15,
wherein the electrical characteristic measuring unit measures a value of the voltage or a value of the current as the electrical characteristic in a discrete manner based on the measurement condition.

19. The battery charger according to claim 15,
wherein the measurement condition is determined for the identification information of the secondary battery, for a type of vehicle which mounts the secondary battery, or for manufacturer information.

20. The battery charger according to claim 15, further comprising
a display unit that displays the state of the secondary battery notified from the determining device.

21. A secondary battery state management method comprising:
allowing a battery charger that determines a measurement condition for a secondary battery and charges the secondary battery to measure an electrical characteristics during charging based on the determined measurement condition; and
allowing a storage server that includes a measurement information storage unit that stores a history of the electrical characteristic for the secondary battery to determine a state of the secondary battery based on the measured electrical characteristic and the history of the electrical characteristic that is stored in the measurement information storage unit and corresponds to the secondary battery.

22. The secondary battery state management method according to claim 21,
wherein when measuring the electrical characteristics, a voltage value between power feeding lines that connect the secondary battery and the battery charger and at least one of a current value that flows through the power feeding lines, power and an electric energy are measured as the electrical characteristics.

23. An electrical characteristics measurement method comprising:
allowing a battery charger that determines a measurement condition for a secondary battery and charges the secondary battery to measure an electrical characteristics during charging of the secondary battery based on the determined measurement condition; and
allowing the battery charger to transmit the measured electrical characteristic of the secondary battery to a determining device that determines a state of the secondary battery based on the received electrical characteristic and a stored history of the electrical characteristic corresponding to the secondary battery.

24. The electrical characteristics measurement method according to claim 23,
wherein when measuring the electrical characteristics, a voltage value between power feeding lines that connect the secondary battery and the battery charger and at least one of a current value that flows through the power feeding lines, power and an electric energy are measured as the electrical characteristics.

25. A non-transitory computer readable information recording medium storing an electrical characteristics measurement program that is mounted on a computer that charges a secondary battery, when executed by a processor, performs a method for:
determining a measurement condition for the secondary battery and measuring an electrical characteristic during charging of the secondary battery based on the determined measurement condition; and transmitting an electrical characteristic of the secondary battery measured to a determining device that determines a state of the secondary battery based on the received electrical characteristic and a stored history of the electrical characteristic corresponding to the secondary battery.

26. The non-transitory computer readable information recording medium according to claim 25,
wherein the electrical characteristics measurement program causes the computer to measure a voltage value between power feeding lines that connect the secondary battery and the battery charger and at least one of a current value that flows through the power feeding lines, power and an electric energy as the electrical characteristics.

* * * * *